(12) United States Patent
Distelhorst et al.

(10) Patent No.: US 8,445,441 B2
(45) Date of Patent: May 21, 2013

(54) INHIBITORS OF BCL-2

(75) Inventors: Clark W. Distelhorst, Shaker Heights, OH (US); Yiping Rong, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/218,818

(22) Filed: Aug. 26, 2011

(65) Prior Publication Data

US 2011/0312896 A1 Dec. 22, 2011

Related U.S. Application Data

(62) Division of application No. 12/190,979, filed on Aug. 13, 2008, now Pat. No. 8,034,779.

(60) Provisional application No. 60/955,520, filed on Aug. 13, 2007.

(51) Int. Cl.
*A61K 38/10* (2006.01)
*A61K 38/16* (2006.01)
*C07K 7/08* (2006.01)
*C07K 14/00* (2006.01)

(52) U.S. Cl.
USPC ....... 514/18.9; 514/21.3; 514/21.4; 514/21.5; 514/21.6; 530/324; 530/326

(58) Field of Classification Search
None
See application file for complete search history.

(56) References Cited

U.S. PATENT DOCUMENTS

| | | | |
|---|---|---|---|
| 5,998,583 A | 12/1999 | Korsmeyer | |
| 6,080,724 A | 6/2000 | Chassaing et al. | |
| 6,492,389 B1 | 12/2002 | Huang et al. | |
| 6,994,979 B2 | 2/2006 | Reed et al. | |
| 7,241,804 B1 | 7/2007 | Hockenberry et al. | |
| 8,034,779 B2 * | 10/2011 | Distelhorst et al. | 514/18.9 |
| 2004/0171809 A1 | 9/2004 | Korsmeyer et al. | |
| 2004/0220097 A1 | 11/2004 | Reed et al. | |
| 2006/0166880 A1 | 7/2006 | Mikoshoba et al. | |
| 2007/0054863 A1 | 3/2007 | Satterthwait et al. | |
| 2007/0072860 A1 | 3/2007 | Bruncko et al. | |

FOREIGN PATENT DOCUMENTS

WO WO 9624846 A1 * 8/1996

OTHER PUBLICATIONS

Rong, et al., "Targeting Bcl-2-IP3 Receptor Interaction to Reverse Bcl-2's Inhibition of Apoptotic Calcium Signals", Jul. 25, 2008, Molecular Cell, vol. 31, pp. 255-265.
Reed, et al., "Apoptosis-based Therapies for Hematologic malignancies", Blood, Jul. 15, 2005, vol. 106, No. 2, pp. 407-418.

* cited by examiner

*Primary Examiner* — Jeffrey E Russel
(74) *Attorney, Agent, or Firm* — Tarolli, Sundheim, Covell & Tummino LLP

(57) ABSTRACT

A purified polypeptide for inhibiting binding of BCL-2 to $IP_3$ receptors includes an amino acid sequence consisting of about 10 to 80 amino acids. The amino acid sequence has a sequence identity at least 90% homologous to a portion of SEQ ID NO:1. The polypeptide inhibits binding of Bcl-2 to $IP_3$ receptors of cells that express $IP_3R$ and Bcl-2 and induces apoptosis in a cell.

12 Claims, 13 Drawing Sheets

Peptide enhance ABT737-induced cell death in CLL cells

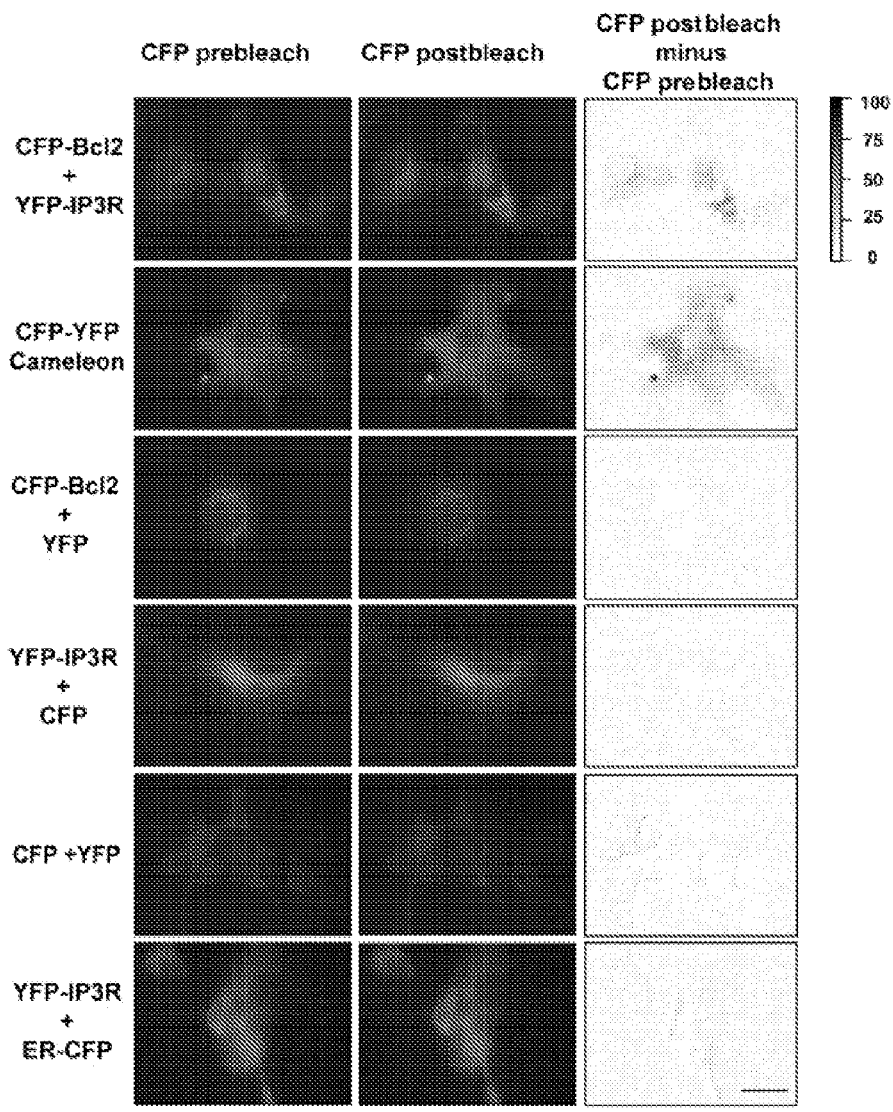
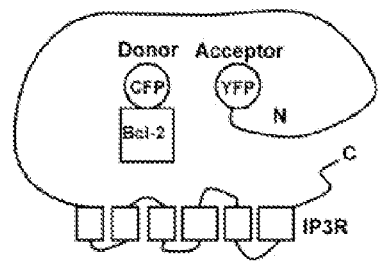
Figs. 1A-B

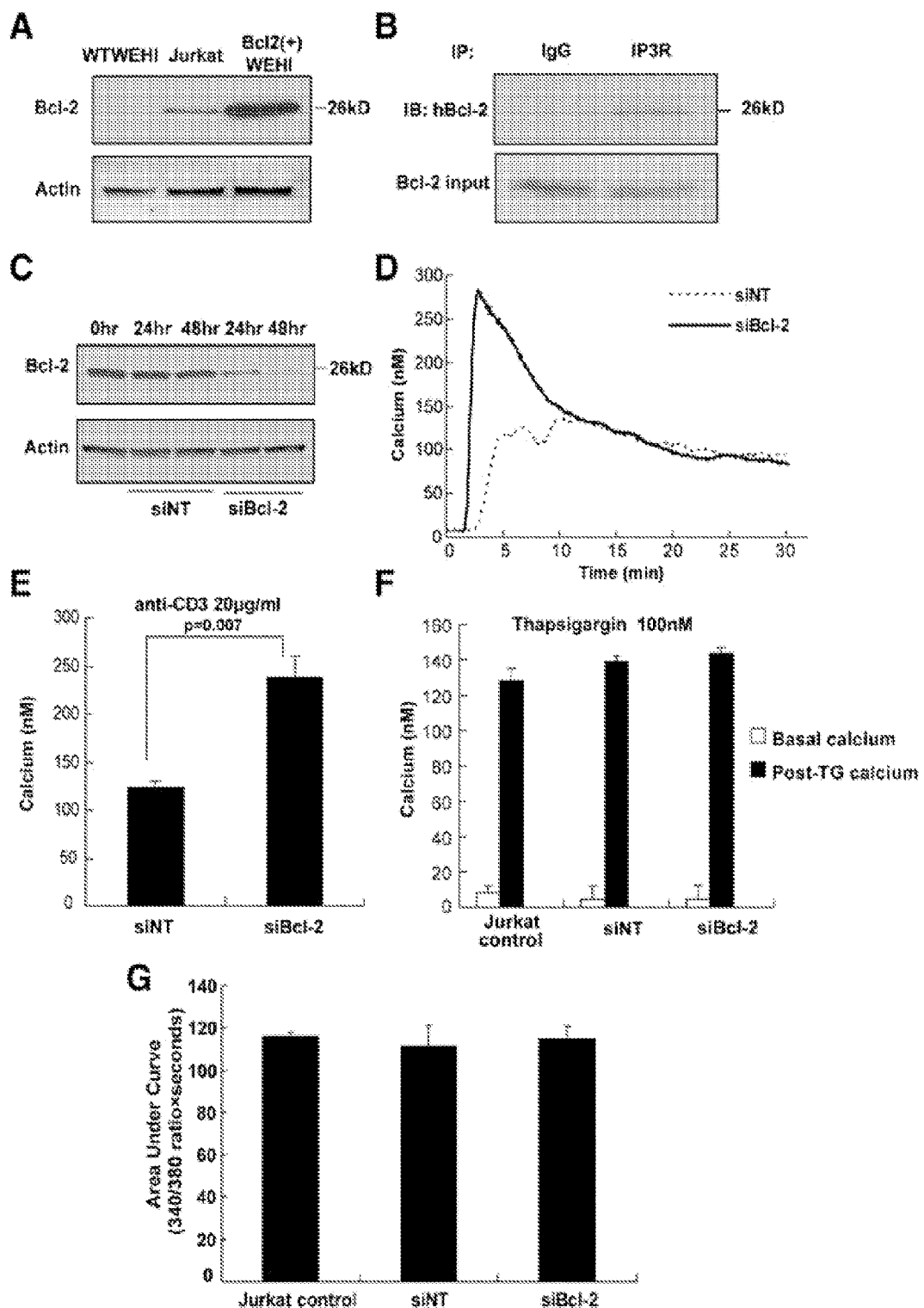
Figs. 2A-G

Figs. 4A-E

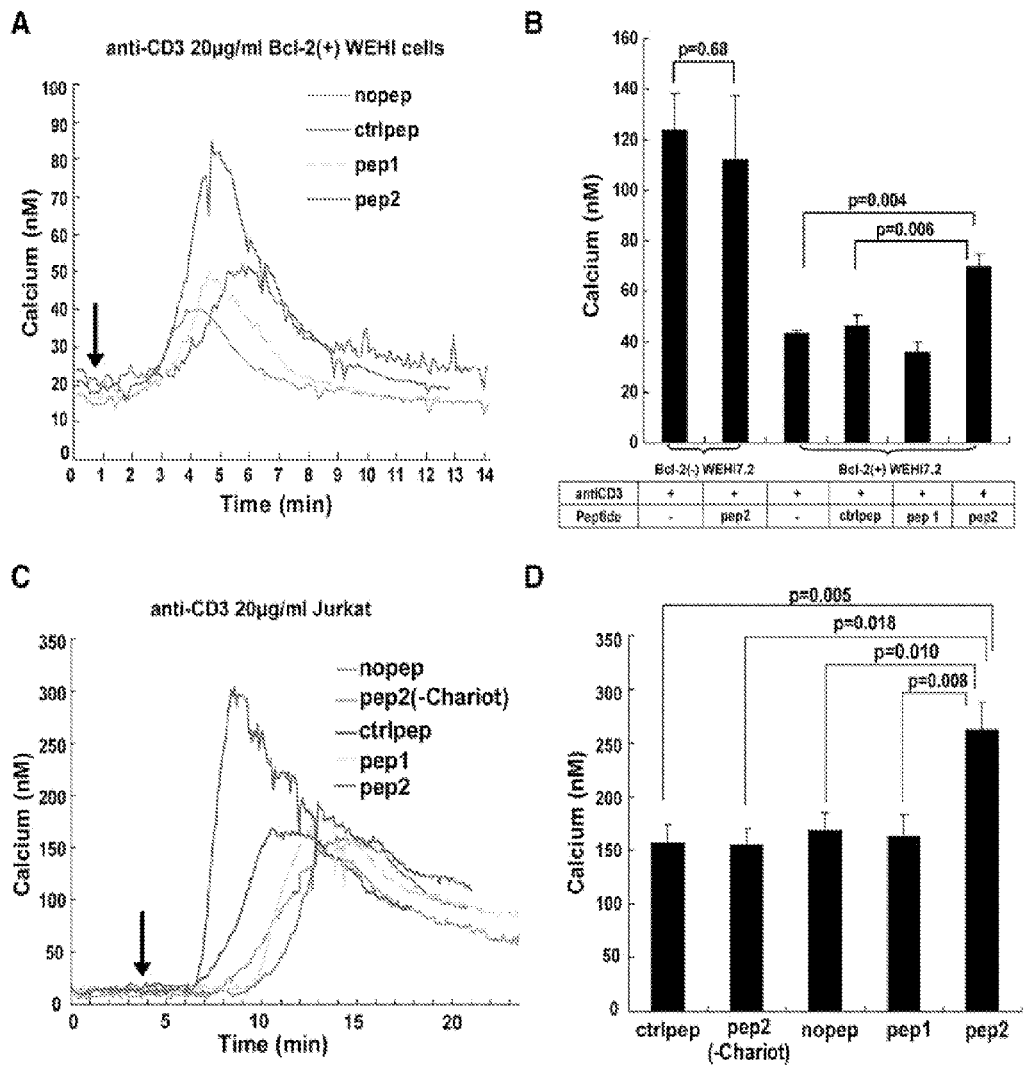
Figs. 6A-D

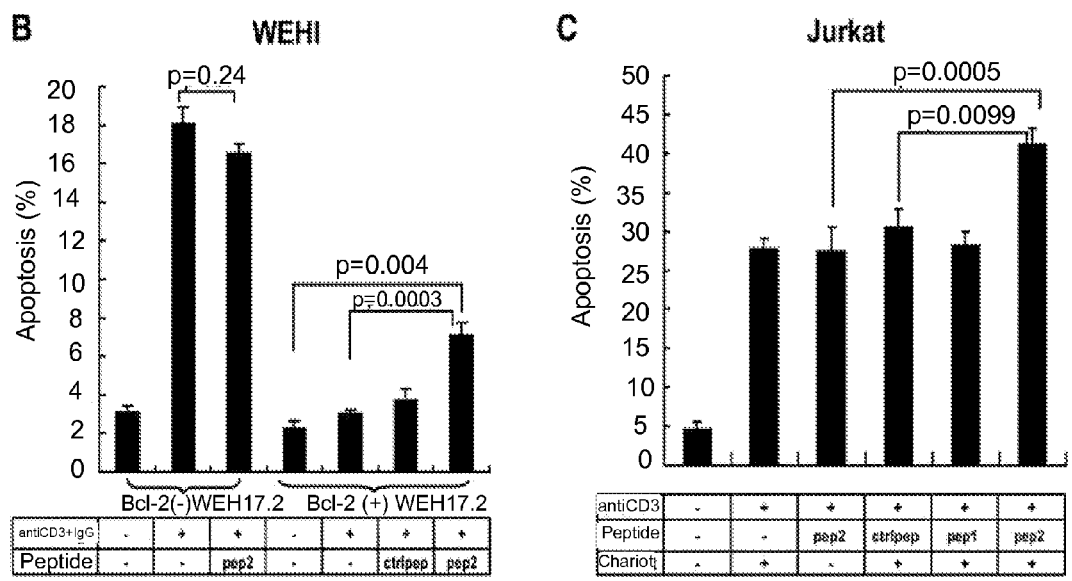
Figs. 7B-C

US 8,445,441 B2

INHIBITORS OF BCL-2

RELATED APPLICATION

This application is a Divisional of U.S. patent application Ser. No. 12/190,979, filed Aug. 13, 2008, now U.S. Pat. No. 8,034,779 which claims the benefit of U.S. Provisional Application No. 60/955,520, filed Aug. 13, 2007, the subject matter of which is incorporated herein by reference in their entirety.

GOVERNMENT FUNDING

This invention was made with government support under Grant No. NIH/NCI RO01 085804 and NIH/NCI SPN00583 awarded by National Institutes of Health. The government has certain rights in the invention.

TECHNICAL FIELD

The present invention relates generally to compounds, and, more particularly, to polypeptides, proteins, and nucleic acids encoding such polypeptides and proteins that can be used to inhibit the interaction of Bcl-2 to the inositol 1,4,5-triphosphate receptor (IP$_3$R).

BACKGROUND OF THE INVENTION

Apoptosis is an important process in the development of cells and is important in maintaining the proper number of cells in the body. Candidates for apoptosis include cells that may be a danger to an organism, such as cells with damaged DNA or cells growing at improper rates. However, apoptosis is also applied to normal cells that have simply become obsolete as organisms grow and develop.

Bcl-2 protein is known to inhibit apoptotic cell death. Bcl-2 protein serves as a check on apoptosis allowing healthy and useful cells to survive. Anti-apoptotic molecules, such as Bcl-2 are often overexpressed in cancer cells and their inhibition is an attractive target for selective killing of tumor cells via induction of apoptosis. Bcl-2 overexpression and/or activation has been correlated with resistance to chemotherapy, to radiotherapy and to development of hormone-resistant tumors. Inhibition of apoptosis by Bcl-2 contributes to cancer by inhibiting cell death. Thus, inhibiting Bcl-2 activity in cancer cells can reduce chemotherapeutic resistance and increase the killing of cancer cells.

The Bcl-2 gene was discovered as the translocated locus in a B-cell leukemia. Bcl-2 contains a single transmembrane domain and is localized within a cell to the outer mitochondrial, nuclear, and endoplasmic reticulum membranes. Bcl-2 was first isolated as a breakpoint rearrangement in human follicular lymphomas. In humans, most follicular B-cell lymphomas contain a chromosomal translocation that moves the gene for Bcl-2 from its normal location to a position within the genes for immunoglobulins. In this new location, higher quantities of Bcl-2 are produced. Since Bcl-2 is a potent pro-survival protein, it shields the cancer cells from apoptotic instruction.

The effector molecules in the apoptotic pathway are a family of enzymes known as the caspases. The Bcl-2 protein suppresses apoptosis by preventing the activation of the caspases that carry out the process. Caspase enzymes are cystein proteases that selectively cleave proteins at sites just C-terminal to aspartate residues. These proteases have specific intracellular targets such as proteins of the nuclear lamina and cytoskeleton. The cleavage of these substrates leads to the demise of a cell.

The inositol 1,4,5-triphosphate (IP$_3$) messenger molecule is water soluble, and can diffuse within the cytosol carrying an activated G protein signal from the cell surface to the endoplasmic reticulum (ER) surface. IP$_3$ binds to an IP$_3$R and induces opening of the channel allowing Ca$^{2+}$ ions to exit from the ER into the cytosol. The released calcium then triggers a mass exodus of cytochrome c from all mitochondria in the cell, thus activating the caspase and nuclease enzymes that finalize the apoptotic process.

It has previously been shown that Bcl-2 interacts with the inositol 1,4,5-triphosphate receptor (IP$_3$R) and inhibits IP$_3$-mediated Ca$^{2+}$ release from the ER, thereby inhibiting anti-CD3 induced apoptosis in immature T cells (JCB 166:193-203, 2004; JCB 172: 127-137, 2006). IP$_3$R have a broad tissue distribution and are mostly found in the cell integrated into the endoplasmic reticulum. The IP$_3$R is a large six transmembrane ligand gated ion channel which mainly transmits calcium ions and thereby facilitates triggers apoptosis.

SUMMARY OF THE INVENTION

The present invention relates to a purified peptide that comprises about 5 to about 80 amino acids and includes an amino acid sequence corresponding to a portion of SEQ ID NO: 1. The peptide can inhibit binding of Bcl-2 to IP$_3$ receptors of cells that express IP$_3$R and Bcl-2. In an aspect of the invention, the purified peptide can be provided in a pharmaceutical composition that includes a pharmaceutically acceptable carrier.

Another aspect of the invention relates to a purified peptide that comprises about 5 to about 80 amino acids and includes an amino acid sequence corresponding to a portion of SEQ ID NO: 1. The peptide can reverse the interaction of Bcl-2 with IP$_3$ receptors of cells that express IP$_3$R and Bcl-2.

A further aspect of the invention relates to a purified peptide that comprises about 5 to about 80 amino acids and includes an amino acid sequence corresponding to a portion of SEQ ID NO:1. The peptide can inhibit binding of Bcl-2 to the activation coupling domain of the IP$_3$R, from 1347aa to 1426aa of cells that express IP$_3$R and Bcl-2.

A still further aspect of the invention relates to a method of inhibiting Bcl-2 binding to IP$_3$ receptor, (IP$_3$R) in a cell. The method comprises contacting a cell population including cells that express IP$_3$R and Bcl-2 with a composition that comprises a biologically effective amount of a peptide. The peptide can include about 5 to about 80 amino acids and can comprise an amino acid sequence corresponding to a portion of SEQ ID NO:1.

Another aspect of the invention relates to a method of reducing chemotherapeutic resistance in a subject. The method comprises administering to cells of the subject expressing IP$_3$R and Bcl-2 a composition comprising a biologically effective amount of a peptide. The peptide can include about 5 to about 80 amino acids and an amino acid sequence corresponding to a portion of SEQ ID NO:1. The subject can also be treated with one or more chemotherapeutic agents.

A still further aspect of the invention relates to a method of inducing apoptosis in a cell expressing Bcl-2 and IP$_3$R. The method includes administering to the cell an effective amount of an agent that inhibits binding of Bcl-2 to IP$_3$R of the cell. The agent can include a peptide, a peptide analogue, or a small molecule mimetic of the peptide.

In an aspect of the invention, the agent can be a peptide and include about 5 to about 80 amino acids and an amino acid sequence corresponding to a portion of SEQ ID NO:1. The peptide can reverse the interaction of Bcl-2 with IP$_3$R of cells that express IP$_3$R and Bcl-2. The peptide can also include an amino acid sequence selected from the group consisting of: SEQ ID NO:1, SEQ ID NO:2, SEQ ID NO:3 as well as an amino acid sequence that facilitates transport of the purified polypeptide across a biological membrane.

In a further aspect of the invention, the method can include administering a second agent to the cells that inhibits binding of Bcl-2 to BH3 pro-apoptotic proteins. The second agent can comprise at least one of a peptide or small molecule. The small molecule can include at least one of a chromene, a thiazolidin, benzenesulfonyl, a benzenesulfonamide, an antimycin, a dibenzodiazocine, a terphenyl, an indole, gossypol, apogossypol, a an epigallocatechingallate, or a theaflavanin. The benzenesulfonamide can include N-(4-(4-(4'-chloro-biphenyl-2-ylmethyl)-piperazin-1-yl)-bezoyl)-4-(3-dimethylamino-1-phenylsulfanylmethyl-propylamino)-3-nitro-benzenesulfonamide or ABT-737.

Yet another aspect of the invention relates to a method of treating a neoplastic disorder in a subject by administering to cells of the subject expressing IP$_3$R and Bcl-2 a composition that comprises a biologically effective amount of a peptide. The peptide can include about 5 to about 80 amino acids and can have an amino acid sequence corresponding to a portion of SEQ ID NO:1. In an aspect of the invention, the method can include the step of treating the subject with one or more chemotherapeutic agents.

A still further aspect of the invention relates to a method of treating a neoplastic disorder in a subject by administering to neoplastic cells of the subject expressing IP$_3$R and Bcl-2 a therapeutically effective amount of a first agent that inhibits binding of Bcl-2 to IP$_3$R of the cells, and a therapeutically effective amount of a second agent that inhibits binding of Bcl-2 to BH3 pro-apoptotic proteins of the cells.

In an aspect of the invention, the first agent can be a peptide, a peptide analogue, or a small molecule mimetic of the peptide. The peptide can include about 5 to about 80 amino acids and an amino acid sequence corresponding to a portion of SEQ ID NO:1. The peptide can reverse the interaction of Bcl-2 with IP$_3$R of cells that express IP$_3$R and Bcl-2. The peptide can also include an amino acid sequence selected from the group consisting of: SEQ ID NO:1, SEQ ID NO:2, SEQ ID NO:3 as well as an amino acid sequence that facilitates transport of the purified polypeptide across a biological membrane.

The second agent can comprise at least one of a peptide or small molecule. The small molecule can include at least one of a chromene, a thiazolidine, a benzenesulfonyl, a benzenesulfonamide, an antimycin, an dibenzodiazocine, a terphenyl, an indole, gossypol, apogossypol, an epigallocatechingallate, or a theaflavanin. The benzenesulfonamide can include N-(4-(4-(4'-chloro-biphenyl-2-ylmethyl)-piperazin-1-yl)-bezoyl)-4-(3-dimethylamino-1-phenylsulfanylmethyl-propylamino)-3-nitro-benzenesulfonamide or ABT-737.

Another aspect of the invention relates to a method of identifying molecules that induce apoptosis. The method includes screening compounds to determine whether they bind to Bcl-2 labeled with an isotope at the same site where IP$_3$R binds wherein the site is different than the BH3 binding site on Bcl-2. Any of the compounds, which bind to Bcl-2 labeled with an isotope at the same site where IP$_3$R binds are assayed to determine whether compound induces apoptosis.

The isotope can be selected from the group consisting of $^{15}$N, $^{13}$C, and $^2$H. The screening can be carried out using high throughput screening. Nuclear magnetic resonance can also used to identify where the compound is binding.

BRIEF DESCRIPTION OF DRAWINGS

Further features of the present invention will become apparent to those skilled in the art to which the present invention relates from reading the following description of the invention with reference to the accompanying drawings.

FIG. 2 illustrates endogenous Bcl-2 Inhibits Anti-CD3-Induced Ca$^{2+}$ Elevation in Jurkat Cells. (A) Bcl-2 levels in wild-type WEHI7.2, Jurkat, and Bcl-2(+) WEHI7.2 cells by immunoblotting. (B) Communoprecipitation of Bcl-2 with IP$_3$R in Jurkat extracts; immunoblot analysis using anti-Bcl-2 antibody. (C) Immunoblot of Bcl-2 in Jurkat extracts 24 and 48 hr after transfection with nontargeting control siRNA (siNT) or Bcl-2 siRNA (siBcl-2). (D) Digital imaging traces (average 160 cells per sample) monitoring Ca$^{2+}$ elevation induced by 20 µg/ml anti-CD3 in the presence of extracellular Ca$^{2+}$. (E) Peak Ca$^{2+}$ elevation induced by 20 µg/ml anti-CD3 in presence of extracellular Ca$^{2+}$ (mean±SEM, three experiments). (F) Peak Ca$^{2+}$ elevation induced by 100 nM thapsigargin, measured fluorometrically in the absence of extracellular Ca$^{2+}$ (mean±SEM, three experiments). (G) Area under the cytosolic Ca$^{2+340}$ nM/380 nM ratio curve in (F) (mean±SEM, three experiments).

FIGS. 6A-D illustrates peptide 2 (SEQ ID NO:3) Reverses Bcl-2's Inhibition of Anti-CD3-Induced Ca$^{2+}$Elevation. (A) Representative Ca$^{2+}$ traces (each the mean of ~65 cells) recording anti-CD3 (arrow, time of addition)-induced Ca$^{2+}$ elevation in Bcl-2(+) WEHI7.2 cells. Peptide (60 µM) uptake was facilitated by Chariot reagent. (B) Peak anti-CD3 induced Ca$^{2+}$ elevation in Bcl-2(-) and Bcl-2(+) WEHI7.2 cells treated with peptides as in (A) [mean±SEM, five experiments for Bcl-2(-) and seven experiments for Bcl-2(+) cells, with mean 68 cells per sample per experiment]. (C) Representative Ca$^{2+}$ traces in Jurkat cells (mean 85 cells each).

Figure 1C:
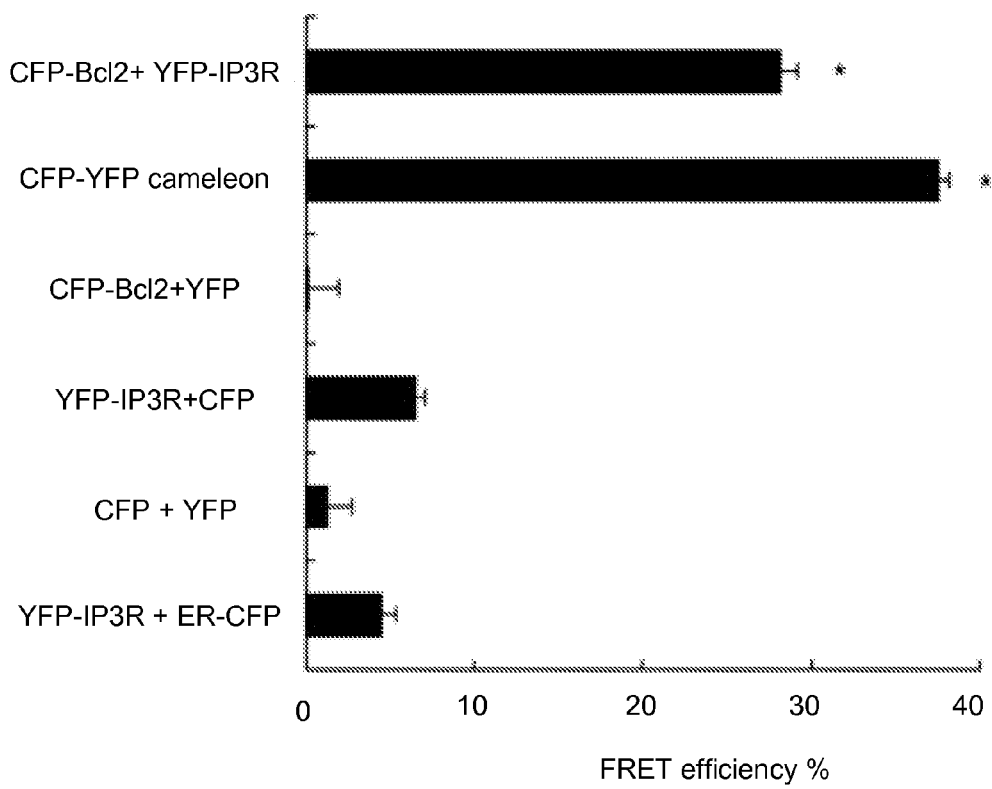
FIG. 1 illustrates FRET Detection of Bcl-2-IP$_3$R Interaction. FRET was detected by the increase of CFP fluorescence following YFP bleaching in COS-7 cells expressing CFP-Bcl-2+YFP-IP$_3$R and CFP-YFP cameleon, but not control combinations of fluorescently tagged proteins. (A) Representative images of CFP fluorescence intensity before and after YFP photobleaching (left and middle columns). Gray value images (right column) were obtained by pixel-by-pixel subtraction of CFP prebleach images from postbleach images, with relative intensity differences represented by the gray scale. Scale bar, 5 mm. (B) Diagram of C-terminal location of CFP and YFP on Bcl-2 and IP$_3$R, respectively. (C) Multiple regions of interest (>60 for each pair of samples) were randomly selected from the CFP and YFP colocalization regions in three individual experiments. FRET efficiency was calculated according to the increase in CFP emission by Volocity software. Symbols represent mean±SEM. *$p<0.01$.

Treatment conditions are the same as in (A), except that a control involving addition of peptide 2 without Chariot reagent has been added. (D) Peak anti-CD3-induced $Ca^{2+}$ elevation in Jurkat cells treated with peptides as in (C) (mean±SEM, seven experiments, mean 81 cells per sample per experiment).

FIG. 7 illustrates peptide 2 Enhances Anti-CD3-Induced Apoptosis in Bcl-2-Positive Cells (A) Typical apoptotic nuclear morphology (arrow, Hoechst 33342 stain) 24 hr after 5 μg/ml anti-CD3 treatment of Jurkat cells. Scale bars, 10 μm. (B) Bcl-2(−) and Bcl-2(+) WEHI7.2 cells were pre-incubated±60 μM peptides plus Chariot reagent and then incubated with 20 μg/ml anti-CD3 for 24 hr. Symbols represent the percentage of cells (mean±SEM) with apoptotic nuclei in three experiments for Bcl-2(−) and five experiments for Bcl-2(+) cells (200 cells counted per coverslip). (C) Jurkat cells were pre-incubated±60 μM peptides±Chariot reagent and then incubated with 5 μg/ml anti-CD3 for 24 hr. Symbols represent the percentage of cells (mean±SEM) with apoptotic nuclei in five experiments (240 cells counted per coverslip).

Figure 8:
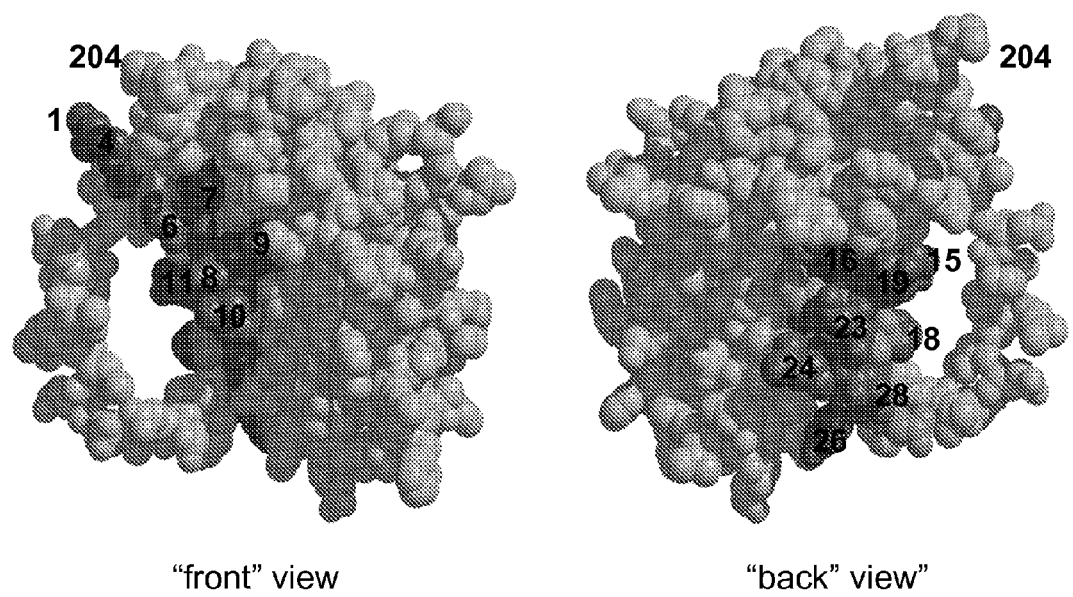

FIG. 8 illustrates a front and back view of the NMR structure of Bcl-2 and the amino acids that are accessible on the BH4 domain in accordance with another aspect of the invention.

Figure 9:
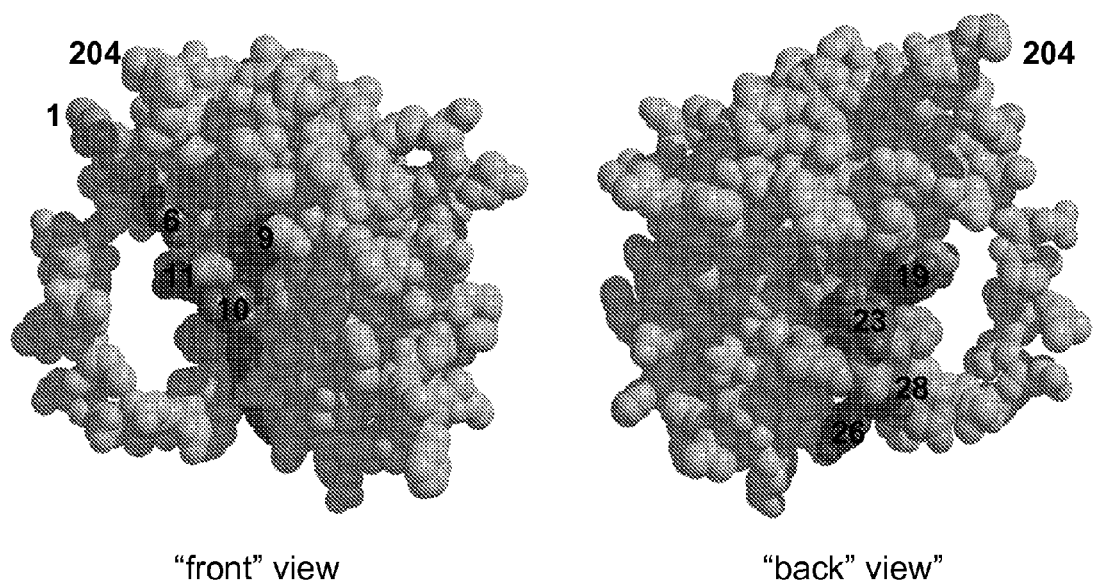

FIG. 9 illustrates a front and back view of the NMR structure of Bcl-2 and the amino acids that are accessible on the BH4 domain in accordance with another aspect of the invention.

Figure 10:
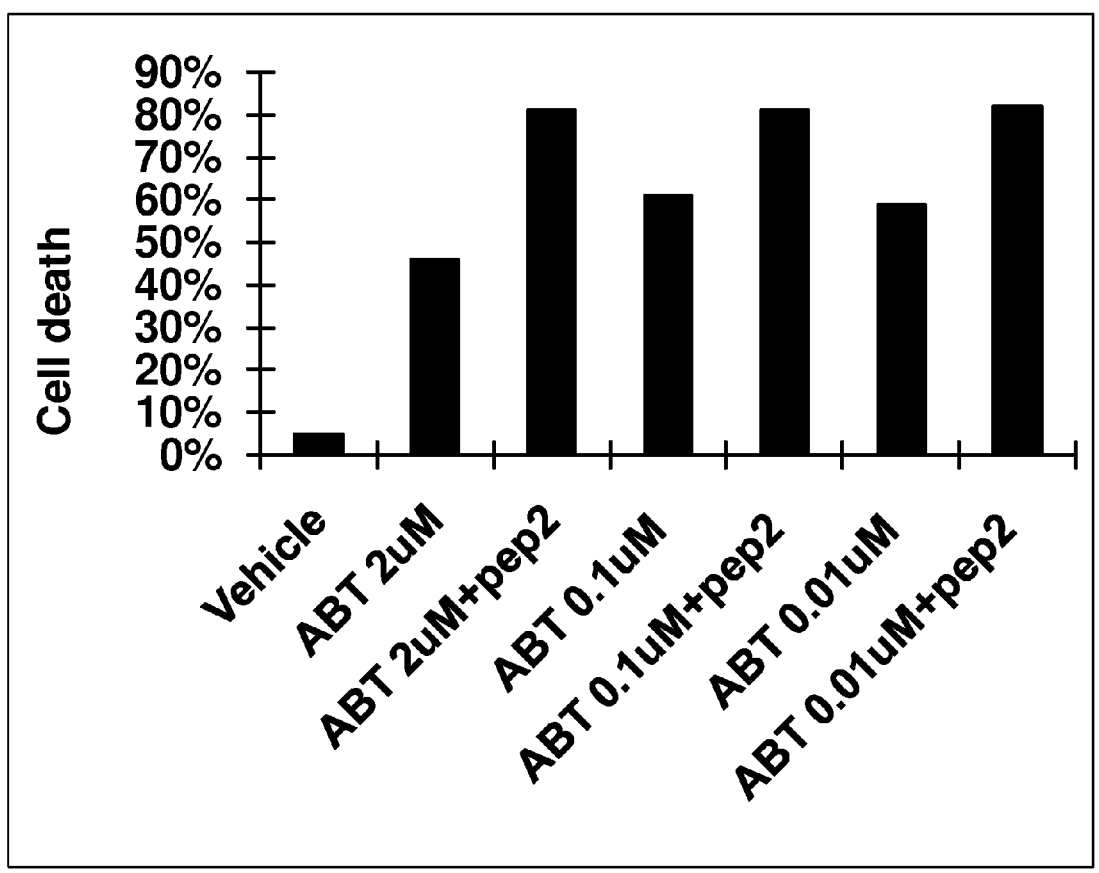

FIG. 10 illustrates a graph comparing the cell death percentage of chronic lymphocytic leukemia cells treated with combinations of ABT-737 and a peptide comprising SEQ ID NO: 3 and controls.

Figure 11:
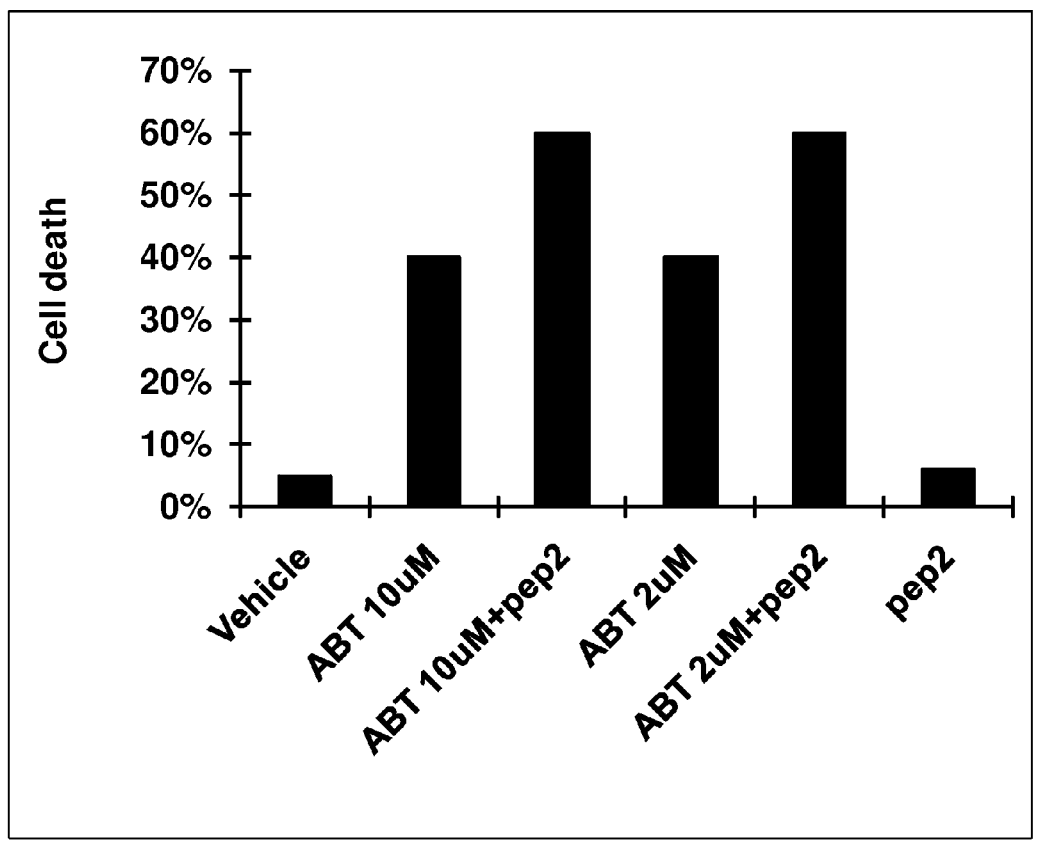

FIG. 11 illustrates a graph comparing the cell death percentage of chronic lymphocytic leukemia cells treated with ABT-737, a peptide comprising SEQ ID NO: 3, combinations thereof, and controls.

DETAILED DESCRIPTION

The following definitions are set forth to illustrate and define the meaning and scope of the various terms used to describe the invention herein.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied.

The terms "peptide(s)", "protein(s)" and "polypeptide(s)" are used interchangeably herein.

The terms "polynucleotide sequence" and "nucleotide sequence" are also used interchangeably herein.

"Recombinant," as used herein, means that a protein is derived from a prokaryotic or eukaryotic expression system.

The term "wild type" refers to the naturally occurring polynucleotide sequence encoding a protein, or a portion thereof, or protein sequence, or portion thereof, respectively, as it normally exists in vivo.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Vectors can include those capable of autonomous replication and/or expression of nucleic acids to which they are linked. Vectors capable of directing the expression of genes to which they are operatively linked are referred to herein as "expression vectors".

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue. The term also covers so-called "leaky" promoters, which regulate expression of a selected nucleic acid primarily in one tissue, but cause expression in other tissues as well.

"Homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

A "chimeric protein" or "fusion protein" is a fusion of a first amino acid sequence encoding a polypeptide with a second amino acid sequence defining a domain (e.g. polypeptide portion) foreign to and not substantially homologous with any domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The "non-human animals" of the invention include mammals such as rats, mice, rabbits, sheep, cats, dogs, cows, pigs, and non-human primates.

The term "isolated" as used herein with respect to nucleic acids, such as DNA or RNA, refers to molecules separated from other DNAs, or RNAs, respectively, that are present in the natural source of the macromolecule. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration other than directly into or locally to the tissue being treated, such that it enters the animal's system and, thus, is subject to metabolism and other like processes, for example, subcutaneous administration.

The phrase "effective amount" as used herein means that the amount of one or more agent, material, or composition comprising one or more agents as described herein which is effective for producing some desired effect in a subject; for example, an amount of the compositions described herein effective to promote apoptosis.

As used herein, "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds described herein may have one or more asymmetrical carbon atoms and therefore include various stereoisomers. All stereoisomers are included within the scope of the present invention.

As used herein, "therapeutically- or pharmaceutically-effective amount" as applied to the disclosed compositions refers to the amount of composition sufficient to induce a desired biological result. That result can be alleviation of the signs, symptoms, or causes of a disease, or any other desired alteration of a biological system. For example, the result can involve a decrease and/or reversal of cancerous cell growth.

The present invention relates to generally agents and methods of substantially inhibiting Bcl-2 binding to inositol 1,4,5-triphosphate receptors (IP$_3$R) as well as to agents and methods of inducing apoptosis in cells expressing Bcl-2 and IP$_3$R and, particularly to inducing apoptosis, in neoplastic cells (e.g., cancer cells) expressing Bcl-2 and IP$_3$R. As used herein, "inhibit", "inhibiting", or "inhibition" includes any measurable reproducible substantial reduction in the interaction between Bcl-2 and IP$_3$R, cancer, or any other activities Bcl-2 may mediate. A substantial reduction is a "reproducible", i.e., consistently observed, reduction in binding.

The mechanism of regulation and interaction between IP$_3$R and Bcl-2 was determined by mapping the interaction region between IP$_3$R and Bcl-2. Bcl-2 was found to bind to Domain 3 (922 amino acid (aa) to 1581 aa) of the IP$_3$R. More specifically, it was found that Bcl-2 interacts directly with the activation coupling domain of the IP$_3$R from 1347 aa to 1426 aa. This internal coupling domain transfers the ligand binding signal from the N-terminal IP$_3$ binding domain to the C-terminal channel domain. The coupling domain is necessary to keep the IP$_3$R channel closed and regulates the activity of the IP$_3$R by binding to regulatory proteins. By binding to this region, Bcl-2 exerts its regulatory effect on IP$_3$-mediated $Ca^{2+}$ signals. The interaction between IP$_3$R and Bcl-2 was also mapped and found that a Bcl-2 mutant containing a BH4 domain deletion does not interact with the IP$_3$R and does not inhibit IP$_3$ mediated ER calcium release. In this way, the BH4 domain of Bcl-2 interacts with the coupling region of IP$_3$R and regulates IP$_3$ mediated $Ca^{2+}$ release from the ER.

Peptides derived from the specific Bcl-2-interacting domain of IP$_3$R, such as a BH4 domain binding peptide including a portion of amino acid SEQ ID NO:1, can mimic IP$_3$Rs binding effect, as will peptide analogs and small molecules designed to mimic the binding properties of the peptides. Peptides, analogs, and small molecules that specifically interact with the BH4 domain of Bcl-2 will effectively induce apoptosis of cancer cells, thus restricting tumor growth. In addition, the peptides provide a molecular basis for developing various agents for treating cancers and other therapeutic applications.

In accordance with an aspect of the present invention, isolated and purified peptides that inhibit binding of Bcl-2 and IP$_3$R can include about 5 to about 80 amino acids and an amino acid sequence corresponding to a portion of ERDRMDENSPLMYHIHLVELLAVCTEGKNVYTEIKCNSLLPLDDIVRVVTHEDCIPEVKI AYINFLNHCYVDTEVEMKEI SEQ ID NO:1. The peptide can contain all or part of the primary structural conformation (i.e., continuous sequence of amino acid residues) of (SEQ ID NO:1).

The peptide can have an amino acid sequence of about 5 to about 80 amino acids (e.g. about 10 to about 30 amino acids) that corresponds to an about 5 to about 80 amino acid portion of the amino acid sequence of human type 1 inositol 1,4,5-triphosphate receptor (IP$_3$R), as recorded in the NCBI protein database under the accession number NP002213. By corresponding to, it is meant the peptide has an amino acid sequence with a sequence identity that is substantially homologous to a portion of the amino acid sequence of the IP$_3$R. By substantially homologous it is meant the polypeptide has at least about 70%, about 80%, about 90%, or about 100% sequence identity with a portion of the amino acid sequence of IP$_3$R.

Examples of peptides that can be used in accordance with the present invention can have an amino acid sequence selected from the group consisting of: SEQ ID NO:1, MDENSPLMYHIHLVELLAVC (SEQ ID NO:2), and NVYTEIKCNSLLPLDDIVRV (SEQ ID NO:3).

Polypeptides comprising portions of SEQ ID NO:1 that exhibit a moderate reduction of Bcl-2 binding to IP$_3$R will still be useful. Nonetheless, preferred peptides comprising SEQ ID NO:1 or fragments of SEQ ID NO:1 will be those that have a more significant ability to inhibit Bcl-2 binding to IP$_3$R. The intention of using peptides that do not substantially inhibit Bcl-2 binding to IP$_3$R is to maintain the biological functions mediated by Bcl-2 binding to IP$_3$R. Therefore, a peptide need only maintain sufficient Bcl-2 binding to IP$_3$R so that a biological response is induced.

The Bcl-2/IP$_3$R inhibiting peptides of the present invention (i.e., peptides that inhibit Bcl-2 binding to IP$_3$R) can be substantially free of other proteins or pathological agents. These peptides can also be a product of mammalian cells, or the product of chemical synthetic procedures or of prokaryotic or eukaryotic host expression (e.g., by bacterial, yeast, higher plant, insect and mammalian cells in culture) of exogenous DNA sequences obtained by genomic or cDNA cloning or by gene synthesis. The products of expression in typical yeast (e.g., *Saccharomyces cerevisiae*) or prokaryote (e.g., *E. coli*) host cells are free of association with any mammalian proteins. The products of expression in vertebrate cells (e.g., non-human mammalian (COS or CHO) and avian) are free of association with any human proteins. Depending upon the host employed, and other factors, peptides of the invention may be glycosylated with mammalian or other eukaryotic carbohydrates or may be non-glycosylated. Peptides of the invention may also include an initial methionine amino acid residue (at position −1 with respect to the first amino acid residue of the polypeptide.)

It will be appreciated that biologically functional equivalents, or even improvements, of the peptide can be made, generally using the peptide of SEQ ID NO:1 as a starting point. Modifications and changes may be made in the structure of such a protein and still obtain a molecule having like or otherwise desirable characteristics. For example, certain amino acids in the protein structure may be substituted without appreciable loss of interactive binding capacity.

Since it is the interactive capacity and nature of a protein that defines that protein's biological functional activity, certain amino acid sequence substitutions can be made in a protein sequence (or of course, the underlying DNA sequence) and nevertheless obtain a protein with like properties. It is thus contemplated that various changes may be made in the sequence of the Bcl-2/IP$_3$R peptides without appreciable loss of their biological utility or activity (e.g., the peptides ability to inhibit binding of Bcl-2 to IP$_3$R).

It is also well understood by the skilled artisan that, inherent in the definition of a "biologically functional equivalent" protein or peptide, is the concept that there is a limit to the number of changes that may be made within a defined portion of the molecule and still result in a molecule with an acceptable level of equivalent biological activity. Biologically functional equivalent proteins and peptides are thus defined herein as those proteins and peptides in which certain, not most or all, of the amino acids may be substituted. Of course, a plurality of distinct proteins/peptides with different substitutions may easily be made and used in accordance with the invention.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine; are defined herein as biologically functional equivalents.

Following the procedures noted in the published application by Alton et al. (WO83/04053), one can readily design and manufacture genes coding for microbial expression of peptides having primary conformations, which differ from that herein specified in terms of the identity of location of one or more residues (e.g., substitutions, terminal and intermediate additions and deletions). Alternately, modification of cDNA may be readily accomplished by well-known site-directed mutagenesis techniques and employed to generate analogs and derivatives of the polypeptide. Such products would share at least one of the biological properties of the Bcl-2/IP$_3$R inhibiting peptide but may differ in others. As examples, projected products of the invention include those which are foreshortened by e.g., deletions; or those which are more stable to hydrolysis (and, therefore, may have more pronounced or longer lasting effects than naturally-occurring); or which have been altered to delete one or more potential sites for glycosylation (which may result in higher activities for yeast-produced products); or which have one or more cysteine residues deleted or replaced by, e.g., alanine or serine residues and are potentially more easily isolated in active form from microbial systems; or which have one or more tyrosine residues replaced by phenylalanine and bind more or less readily to target proteins or to receptors on target cells.

The Bcl-2/IP$_3$R peptide of the present invention can also be in the form of a conjugate protein or drug delivery construct having a transport subdomain(s) or moiety(ies) (i.e., transport moieties). The transport moieties can facilitate uptake of the peptide into a mammalian (i.e., human or animal) tissue or cell. The transport moieties can be covalently linked to the peptide. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the peptide.

The transport moieties can be repeated more than once in the peptide. The repetition of a transport moiety may affect (e.g., increase) the uptake of the peptide by a desired cell. The transport moiety may also be located either at the amino-terminal region of an active agent or at its carboxy-terminal region or at both regions.

In an aspect of the invention, the transport moiety can include at least one transport peptide sequence that allows the Bcl-2/IP$_3$R inhibiting peptide to penetrate into the cell by a receptor-independent mechanism. Examples of transport sequences that can be used in accordance with the present invention include a Tat-mediated protein delivery sequence (Vives (1997) 272: 16010-16017), polyarginine sequences (Wender et al. 2000, PNAS 24: 13003-13008) and antennapedia (Derossi (1996) J. Biol. Chem. 271: 18188-18193). Other examples of known transport moieties, subdomains and the like are described in, for example, Canadian patent document No. 2,301,157 (conjugates containing homeodomain of antennapedia) as well as in U.S. Pat. Nos. 5,652, 122, 5,670,617, 5,674,980, 5,747,641, and 5,804,604, all of which are incorporated herein by reference in their entirety. Still other examples of transport moieties include conjugates containing amino acids of Tat HIV protein, herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

In addition, the transport moiety(ies) can include polypeptides having a basic amino acid rich region covalently linked to the Bcl-2/IP$_3$R inhibiting peptide. As used herein, the term "basic amino acid rich region" relates to a region of a protein with a high content of the basic amino acids such as arginine, histidine, asparagine, glutamine, lysine. A "basic amino acid rich region" may have, for example 15% or more (up to 100%) of basic amino acids. In some instance, a "basic amino acid rich region" may have less than 15% of basic amino acids and still function as a transport agent region. In one example, a basic amino acid region will have 30% or more (up to 100%) of basic amino acids.

In one example, the Bcl-2/IP$_3$R inhibiting peptide can be provided as a fusion protein (polypeptide) that includes of a carboxy terminal Bcl-2/IP$_3$R inhibiting peptide in accordance with the present invention and an amino terminal transport moiety. The amino terminal transport moiety can be a transport subdomain of HIV (e.g., HIV-1) Tat protein, homeoprotein transport sequence, a Histidine tag or a functional derivative and analogues thereof (i.e. pharmaceutically acceptable chemical equivalents thereof). In another example, the fusion protein (polypeptide) can include a carboxy terminal Bcl-2/IP$_3$R inhibiting peptide and an amino terminal transport moiety that includes a homeodomain of antennapedia.

In another aspect of the invention, the peptide of the present invention can be non-covalently linked to a transport moiety or transfection agent. An example of a non-covalently linked peptide transfection agent is the Chariot protein delivery system (See U.S. Pat. No. 6,841,535; Morris et al. (1999) J. Biol.

Chem. 274(35):24941-24946; and Morris et al. (2001) Nature Biotech. 19:1173-1176), all herein incorporated by reference in their entirety.

The Chariot protein delivery system includes a peptide transfection agent that can non-covalently complex with the Bcl-2/IP$_3$R inhibiting peptide of the present invention. Upon cellular internalization, the transfection agent dissociates and the peptide is free to function. The complex of the Chariot transfection peptide and the Bcl-2/IP$_3$R inhibiting peptide of present invention can be delivered to and internalized by mammalian cells allowing for higher dosages of therapeutics to be delivered to the site of pathology.

In accordance with another aspect of the present invention, the Bcl-2/IP$_3$R peptide can be provided in a pharmaceutically acceptable carrier. The pharmaceutical compositions will generally comprise an effective amount of Bcl-2/IP$_3$R inhibiting peptide, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

The Bcl-2/IP$_3$R inhibiting polypeptide of the present invention will most often be formulated for parenteral administration, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains such a polypeptide or immunoconjugate as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

Compositions of the Bcl-2/IP$_3$R inhibiting peptide can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Carriers can include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the Bcl-2/IP$_3$R inhibiting peptide can be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

Pharmaceutical compositions in accordance with the invention can generally include an amount of the Bcl-2/IP$_3$R inhibiting polypeptide admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards. Upon formulation, the polypeptide or conjugate solutions will be administered in a manner compatible with the dosage formulation and in such amount as is therapeutically effective.

Formulations of polypeptides comprising the Bcl-2/IP$_3$R inhibiting polypeptide are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, topical formulations, liposomal forms and the like. The type of form for administration will be matched to the disease or disorder to be treated.

Pharmaceutical "slow release" capsules or "sustained release" compositions or preparations may be used and are generally applicable. Slow release formulations are generally designed to give a constant drug level over an extended period and may be used to deliver the Bcl-2/IP$_3$R inhibiting peptide in accordance with the present invention. The slow release formulations are typically implanted in the vicinity of the disease site, for example, at the site of a tumor.

Examples of sustained-release preparations include semipermeable matrices of solid hydrophobic polymers containing the polypeptide or immunoconjugate, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773, 919; copolymers of L-glutamic acid and y ethyl-L-glutamate; non-degradable ethylene-vinyl acetate; degradable lactic acid-glycolic acid copolymers, such as the LUPRON DEPOT (injectable microspheres composed of lactic acid-glycolic acid copolymer and leuprolide acetate); and poly-D-(–)-3-hydroxybutyric acid.

While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thiodisulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the Bcl-2/IP$_3$R inhibiting polypeptide. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

A population of cells or tissues that express IP$_3$R can and Bcl-2 thus be contacted with a biologically effective amount of peptides or proteins comprising an amino acid sequence corresponding to a portion of SEQ ID NO:1 in a pharmaceutical carrier under conditions effective to substantially inhibit Bcl-2 binding to IP$_3$R.

The present invention additionally relates to a method of inhibiting Bcl-2 binding to IP$_3$R, the method includes contacting a cell population including cells that express IP$_3$R and Bcl-2 with a composition that comprises a biologically effective amount of a peptide. The polypeptide can comprise about 5 to about 80 amino acids and can include an amino acid sequence corresponding to a portion of SEQ ID NO:1.

A further aspect of the present invention relates to nucleic acid sequences useful in facilitating expression in prokaryotic or eukaryotic host cells of polypeptides or proteins comprising at least a portion of the polypeptide with the ability to substantially inhibit Bcl-2 binding to the IP$_3$ receptor. Such nucleic acid molecules may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. There may also be multiple coding sequences that, as a result of the redundancy or degeneracy of the genetic code, encodes the same polypeptide as such polynucleotides.

Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histidine, for (or by) an electronegative residue, e.g., glutamine or aspartine; or (d) a residue having a bulky side chain, e.g., phenylalanine, for (or by) one not having a side chain, e.g., glycine.

Shorter oligonucleotides that encode or hybridize with nucleic acids that encode fragments of polypeptide can be used as probes, primers, or antisense molecules. Longer polynucleotides that encode or hybridize with nucleic acids that encode fragments of the polypeptide can also be used in various aspects of the invention. Nucleic acids encoding fragments of the polypeptide can be made by enzymatic digestion (e.g., using a restriction enzyme) or chemical degradation of the full-length polypeptide.

Nucleic acids that hybridize under stringent conditions to one of the foregoing nucleic acids can also be used in the invention. For example, such nucleic acids can be those that hybridize to one of the foregoing nucleic acids under low stringency conditions, moderate stringency conditions, or high stringency conditions are within the invention.

Nucleic acid molecules encoding a polypeptide conjugate, such as a fusion protein, may also be used in the invention. Such nucleic acids can be made by preparing a construct (e.g., an expression vector) that expresses the polypeptide fusion protein when introduced into a suitable host. For example, such a construct can be made by ligating a first polynucleotide encoding the polypeptide fused in frame with a second polynucleotide encoding another protein such that expression of the construct in a suitable expression system yields a fusion protein.

The oligonucleotides of the invention can be DNA or RNA or chimeric mixtures or derivatives or modified versions thereof, single-stranded or double-stranded. Such oligonucleotides can be modified at the base moiety, sugar moiety, or phosphate backbone, for example, to improve stability of the molecule, hybridization, etc. Oligonucleotides within the invention may additionally include other appended groups such as peptides (e.g., for targeting host cell receptors in vivo), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. USA 84:648-652; PCT Publication No. WO 88/09810, published Dec. 15, 1988), hybridization-triggered cleavage agents. (See, e.g., Krol et al. (1988) BioTechniques 6:958-976) or intercalating agents. (See, e.g., Zon (1988) Pharm. Res. 5:539-549). To this end, the oligonucleotides may be conjugated to another molecule, e.g., a peptide, hybridization triggered cross-linking agent, transport agent, hybridization-triggered cleavage agent, etc.

The DNA sequences provided by the invention are useful in generating new and useful viral and circular plasmid DNA vectors, new and useful transformed and transfected prokaryotic and eukaryotic host cells (including bacterial and yeast cells and mammalian cells grown in culture), and new and useful methods for cultured growth of such host cells capable of expression of the Bcl-2/IP$_3$R inhibiting polypeptide and its related products.

The use of recombinant DNA techniques to achieve such ends is now standard practice to those of skill in the art. These methods include, for example, in vitro recombinant DNA techniques, synthetic techniques and in vivo recombination/genetic recombination. DNA and RNA synthesis may, additionally, be performed using an automated synthesizers.

Once the desired coding region has been produced, an expression vector is created. Expression vectors contain one or more promoters upstream of the inserted DNA regions that act to promote transcription of the DNA and to thus promote expression of the encoded recombinant protein. This is the meaning of "recombinant expression".

In accordance with another aspect of the present invention, the Bcl-2/IP$_3$R inhibiting peptide may be used to treat animals and patients with a number of neoplastic diseases, including but not limited to lymphoma (e.g. follicular B-cell lymphoma), leukemia, melanoma, breast, prostate, and lung carcinomas, as well as schizophrenia and autoimmunity. The Bcl-2/IP$_3$R inhibiting peptide can also be used for reducing resistance to conventional cancer treatment.

In designing appropriate doses of the Bcl-2/IP$_3$R inhibiting peptide for the treatment of vascularized tumors, one may readily extrapolate from the knowledge in the literature in order to arrive at appropriate doses for clinical administration. To achieve a conversion from animal to human doses, one would account for the mass of the agents administered per unit mass of the experimental animal and, preferably, account for the differences in the body surface area (m$^2$) between the experimental animal and the human patient. All such calculations are well known and routine to those of ordinary skill in the art.

The intention of the therapeutic regimens of the present invention is generally to produce significant anti-neoplastic effects while still keeping the dose below the levels associated with unacceptable toxicity. In addition to varying the dose itself, the administration regimen can also be adapted to optimize the treatment strategy. In administering the particular doses, one can provide a pharmaceutically acceptable composition (according to FDA standards of sterility, pyrogenicity, purity and general safety) to the patient systemically. Intravenous injection is generally preferred. Continuous infusion over a time period of about 1 or 2 hours or so is also contemplated.

The Bcl-2/IP$_3$R inhibiting polypeptide of the present invention may also be delivered in combination with a second agent that induces apoptosis in neoplastic cells. Although many anti-cancer agents may have, as part of their mechanism of action, an apoptosis-inducing effect, certain agents have been discovered, designed or selected with this as a primary mechanism, as described below.

In an aspect of the invention, the second agent can be a small-molecule inhibitor that directly binds Bcl-2/IP$_3$R or related antiapoptotic proteins and inhibits the Bcl-2-BH3 domain binding to BH3 domain proteins or BH3 only molecules, such as BID, NOXA, PUMA, BIK, BIM, and BAD (i.e., a Bcl-2/BH3 inhibitor). By targeting two different regions of Bcl-2 involved in apoptosis inhibition with the Bcl-2/IP$_3$R peptide of the present invention and an inhibitor of Bcl-2 to BH3 domain proteins, the proapoptotic activity of the Bcl-2/BH3 inhibitors and the Bcl-2/IP$_3$R peptides are enhanced.

One example of a small molecule inhibitor is gossypol or 1,6,7,1',6',7'-Hexahydroxy-5,5'-diisopropyl-3,3'-dimethyl-[2,2']binaphthalenyl-8,8'-dicarbaldehyde. Gossypol has the following formula:

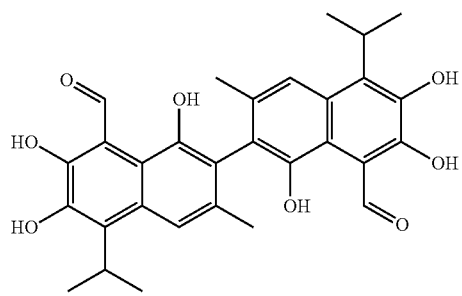 [SMILES: Cc1cc2c(C(C)C)c(O)c(O)c(C=O)c2c(O)c1-c1c(C)cc2c(C(C)C)c(O)c(O)c(C=O)c2c1O]

Gossypol is found in cottonseeds originally used as an herbal medicine in China. Gossypol binds via a conserved 16 amino acid motif called a Bcl-2 homology-3 (BH3) domain found on the surface of antiapoptotic Bcl-2 family proteins. This binding pocket represents a regulatory site, where endogenous antagonists dock onto Bcl-2 and related antiapoptotic proteins, negating their cytoprotective activity. Proof of concept experiments using BH3 peptides have suggested that compounds docking at this regulatory site on Bcl-2 and Bcl-XL effectively promote apoptosis of lymphoma and leukemia cells in vivo in mice.

Gossypol interacts with the BH3-binding pockets of 4 antiapoptotic Bcl-2 family proteins tested to date, Bcl-2, Bcl-X$_L$, Bcl-B, and Bfl-1, displacing BH3 peptides with an inhibitory concentration of 50% (IC$_{50}$) of about 0.5 µM.

Another example of small molecule inhibitor of Bcl-2 is a semisynthetic analog of gossypol known as apogossypol or 5,5'-Diisopropyl-3,3'-dimethyl-[2,2]binaphthalenyl-1,6,7,1', 6',7'-hexaol, which has the following general formula:

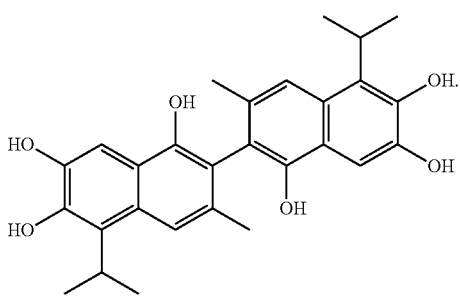

Other examples of chemical inhibitors of Bcl-2, Bcl-$X_L$, and Mcl-1 have been reported, most of which are currently in preclinical evaluation, including: chromenes or chromene derivatives, such as HA14-1 or 2-amino-6-bromo-4-cyano-ethoxycarbonyl-methyl)-4H-chromene-3-carboxylic acid ethyl ester or other compounds disclosed in U.S. Pat. No. 6,492,389; thiazolidins or thiazolidin derivatives, such as BH3I-1 or (2-[5-(4-Bromo-benzylidene)-4-oxo-2-thioxo-thiazolidin-3-yl]-3-methyl-butyric acid); benzene sulfonyl derivatives, such as BH3I-2 or (5-chloro-N-[2-chloro-4-(4-chloro-benzenesulfonyl)-phenyl]-2-hydroxy-3-iodo-benzamide); antimycin analogs, such as 3-(3-Formylamino-2-hydroxy-benzoylamino)-2,6-dimethyl-4,9-dioxo-8-pentyl-[1,5]dioxonane-7-carboxylic acid isopropyl ester or Antimycin A3, and antimycin analogues disclosed in U.S. Pat. No. 7,241,804 (e.g., structures I-V); theaflavins, such as 3,4,6-trihydroxy-1-(3,5,7-trihydroxy-chroman-2-yl)-benzocyclohepten-5-one; epigallechatechins (EGCGs), such as 3,4,5-Trihydroxy-benzoic acid 5,7-dihydroxy-2-(3,4,5-trihydroxy-phenyl)-chroman-3-yl ester; benzenesulfonamides, such as ABT-737 or N-[4-[4-[4-(4'-Chloro-biphenyl-2-ylmethyl)-piperazin-1-yl]-benzoyl)-4-(3-dimethylamino-1-phenylsulfanylmethyl-propylamino)-3-nitro-benzenesulfonamide (a synthetic small-molecule inhibitor produced by NMR-guided, structure-based drug design (Abbott Laboratories, North Chicago, Ill.); indoles, such as GX15-070 (Gemin X, Montreal, Canada) or 2-[5-(3,5-Dimethyl-1H-pyrrol-2-ylmethylene)-4-methoxy-5H-pyroll-2-yl]-1H-indole; dibenzodiazocines, such as 2,9-Dimethoxy-11,12-dihydro-dibenzo[c,g][1,2]diazocine 5,6-dioxide; and terphenyl derivatives, such as a compound having the following formula:

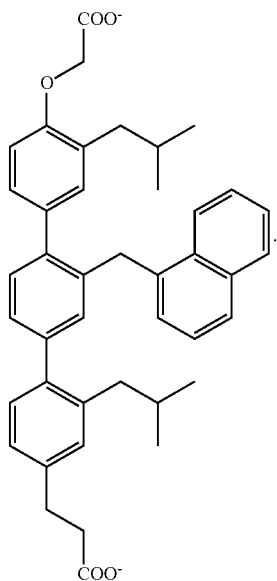

Side-by-side comparisons of these chemical inhibitors of antiapoptotic Bcl-2 proteins have not been reported, but their approximate rank-order potency with respect to affinity for the BH3 pocket of Bcl-2 or Bcl-$X_L$ appears to be ABT-737>EGCG>theaflavins>gossypol>apogossypol>HA14-1 and antimycin. Accordingly, in one example the second agent administered to the cells is ABT-737 or N-(4-[4-(4'-Chloro-biphenyl-2-ylmethyl)-piperazin-1-yl]-benzoyl)-4-(3-dimethylamino-1-phenylsulfanylmethyl-propylamino)-3-nitro-benzenesulfonamide.

The Bcl-2/$IP_3$R inhibiting peptide based treatment methods of the present invention may also be combined with any other methods generally employed in the treatment of the particular tumor, disease or disorder that the subject exhibits. So long as a particular therapeutic approach is not known to be detrimental to the patient's condition in itself, and does not significantly counteract the Bcl-2/$IP_3$R inhibiting peptide based treatment, its combination with the present invention is contemplated.

In another aspect of the invention, the Bcl-2/$IP_3$R inhibiting peptide can be co-administered with one or more anti-cellular agents. Examples anti-cellular agents include chemotherapeutic agents, as well as cytotoxins. Chemotherapeutic agents that can be used include: hormones, such as steroids; anti-metabolites, such as cytosine arabinoside, fluorouracil, methotrexate or aminopterin; anthracyclines; mitomycin C; vinca alkaloids; demecolcine; etoposide; mithramycin; anti-tumor alkylating agents, such as chlorambucil or melphalan. Other embodiments can include agents such as cytokines. Basically, any anti-cellular agent may be used.

Many forms of cancer have reports of mutations in tumor suppressor genes, such as p53. Inactivation of p53 results in a failure to promote apoptosis. With this failure, cancer cells progress in tumorigenesis, rather than become destined for cell death. Thus, delivery of tumor suppressors is also contemplated for use in the present invention to stimulate cell death. Examples of tumor suppressor agents are disclosed in U.S. Pat. Nos. 5,747,469; 5,677,178; and 5,756,455; 5,750,400; 5,654,155; 5,710,001; 5,756,294; 5,709,999; 5,693,473; 5,753,441; 5,622,829; and 5,747,282 (each incorporated herein by reference), Other compositions that may be administered with the Bcl-2/$IP_3$R inhibiting peptide, include genes encoding the tumor necrosis factor related apoptosis inducing ligand termed TRAIL, and the TRAIL polypeptide (U.S. Pat. No. 5,763,223; incorporated herein by reference); the 24 kD apoptosis-associated protease of U.S. Pat. No. 5,605,826 (incorporated herein by reference); Fas-associated factor 1, FAF1 (U.S. Pat. No. 5,750,653; incorporated herein by reference). Also contemplated for use in these aspects of the present invention is the provision of interleukin-1p-converting enzyme and family members, which are also reported to stimulate apoptosis It will be appreciated that the therapeutic agents administered with the Bcl-2/$IP_3$R inhibiting polypeptide are not limited to the therapeutic agents described above, and that other therapeutic agents and other agents, which do not have therapeutic properties, can be used.

In another aspect of the invention, to aid in the characterization and optimization of compounds that can inhibit binding of Bcl-2-family proteins to $IP_3$R, structure-based drug design has become a useful tool. Solution nuclear magnetic resonance (NMR) techniques can be used to map the interactions between the BH4 domain of the Bcl-2-family protein and chemical compounds that target these anti-apoptotic proteins. NMR chemical shift perturbation is an efficient tool for rapid mapping of interaction interfaces on proteins. Structure-activity relationships (SAR) can be obtained by using nuclear magnetic resonance (NMR), using the method known as "SAR by NMR" (Shuker et al., 1996, *Science* 274:1531; Lugovskoy et al., 2002, *J Am Chem Soc* 124:1234). SAR by NMR can be used to identify, optimize and link together small organic molecules that bind to proximal subsites of a protein to produce high-affinity ligands.

In using NMR to structurally characterize protein-protein and ligand-protein interactions, isotope labeling can result in increased sensitivity and resolution, and in reduced complexity of the NMR spectra. The three most commonly used stable isotopes for macromolecular NMR are $^{13}$C, $^{15}$N and $^{2}$H. Isotope labeling has enabled the efficient use of heteronuclear multi-dimensional NMR experiments, providing alternative approaches to the spectral assignment process and additional structural constraints from spin-spin coupling. Uniform isotope labeling of the protein enables the assignment process through sequential assignment with multidimensional triple-resonance experiments and supports the collection of conformational constraints in de novo protein structure determinations (Kay et al., 1990 *J Magn Reson* 89:496; Kay et al., 1997, *Curr Opin Struct Biol* 7:722). These assignments can be used to map the interactions of a ligand by following chemical-shift changes upon ligand binding. In addition, intermolecular NOE (nuclear Overhauser effect) derived inter-molecular distances can be obtained to structurally characterize protein-ligand complexes.

In addition to uniform labeling, selective labeling of individual amino acids or labeling of only certain types of amino acids in proteins can result in a dramatic simplification of the spectrum and, in certain cases, enable the study of significantly larger macromolecules. For example, the methyl groups of certain amino acids can be specifically labeled with $^{13}$C and $^{1}$H in an otherwise fully $^{2}$H-labeled protein. This results in well resolved heteronuclear [$^{13}$C,$^{1}$H]-correlation spectra, which enables straightforward ligand-binding studies either by chemical shift mapping or by protein methyl-ligand inter-molecular NOEs, thus providing key information for structure-based drug design in proteins as large as 170 kDa (Pellecchia et al., 2002, *Nature Rev Drug Discovery* 1:211). 2D [$^{13}$C, $^{1}$H]-HMQC (heteronuclear multiple quantum coherence) and $^{13}$C-edited [$^{1}$H,$^{1}$H]-NOESY NMR experiments on a ligand-receptor complex can be used to detect binding, determine the dissociation constant for the complex, and provide a low-resolution model based on the available three-dimensional structure of the target, thus revealing the relative position of the ligand with respect to labeled side-chains.

Thus, NMR can be used to identify molecules that induce apoptosis. Compounds can be screened for binding to labeled BH4 domain of Bcl-2, for example. Such labels include $^{15}$N and $^{13}$C. The interaction between the compound and the BH4 domain of Bcl-2, and therefore its ability to induce apoptosis, are determined via NMR.

EXAMPLES

The examples demonstrate that (1) endogenous Bcl-2 in Jurkat cells, which is expressed at levels much lower than exogenously expressed Bcl-2, interacts with IP$_3$Rs and that siRNA-mediated knockdown of Bcl-2 enhances TCR-mediated Ca$^{2+}$ elevation; (2) Bcl-2 and IP$_3$Rs interact in intact cells; and (3) an inhibitory peptide designed by mapping a Bcl-2 interacting site on IP$_3$R abrogates Bcl-2-IP$_3$R interaction. This peptide not only reversed Bcl-2's inhibitory effect on IP$_3$R channel opening in artificial lipid bilayers, but also reversed Bcl-2's inhibitory effect on TCR-induced Ca$^{2+}$ elevation and apoptosis within cells, indicating that the interaction of Bcl-2 with IP$_3$Rs contributes to Bcl-2's inhibitory effect on proapoptotic Ca$^{2+}$ signals.

Example 1

Bcl-2 Interacts with IP$_3$R in Cells

FRET between Bcl-2 and IP$_3$Rs was measured by acceptor photobleaching in fixed cells, which measures dequenching of donor (CFP) emission by acceptor (YFP) photobleaching (Hummer et al., 2003, J. Biol. Chem. 278, 49386-49400; Karpova et al., 2003, J. Microsc. 209, 56-70; Li et al., 2005, J. Biol. Chem. 280, 23945-23959), and by threecube FRET (two-color ratio imaging) in live cells (Erickson et al., 2001, Neuron 31, 973-985). In the first method, YFP-IP$_3$R type 1 was used as acceptor and CFP-Bcl-2 was used as donor (FIG. 1A). Fluorophores were tagged to the cytoplasmic N terminus of both proteins (FIG. 1B). When transiently expressed in COS-7 cells, using relatively low concentrations of expression vectors, CFPBcl-2 and YFP-IP$_3$R were colocalized on the ER with a small fraction of CFP-Bcl-2 localized without YFP-IP$_3$R to mitochondria. Regions where CFP and YFP colocalized were selected for FRET efficiency calculation; thus the calculated FRET efficiencies only represent the efficiencies in the regions where YFP fusions and CFP fusions colocalize, reducing the contribution from CFP on mitochondria. A cameleon Ca$^{2+}$ sensor served as positive control (Miyawaki et al., 1997, Nature 388, 882-887). CFP+YFP-IP$_3$R, YFP+CFP-Bcl-2, and CFP+YFP were negative controls, along with CFP targeted to the cytoplasmic face of the ER (ER-CFP)+YFP-IP$_3$R. ER-CFP localizes to the ER, serving as a negative control to exclude the possibility that FRET arising from the CFP-Bcl-2 and YFP-IP$_3$R pair is merely due to the expression of fluorescently tagged proteins in the same location. After 30 min photobleaching with the YFP excitation fluorescence light, the CFP channel fluorescence intensity increased in both CFP-Bcl-2+YFP-IP$_3$R and CFP-YFP cameleon cells, but not in negative controls (FIG. 1A). The CFP donor dequenching effect was clearly shown by subtracting prebleaching images from postbleaching images through pixel-by-pixel calculation (FIG. 1A, CFP postbleach minus CFP prebleach). The CFP signal increased an average of 28%±1% in YFP-IP$_3$R+CFP-Bcl-2 cells and 37%±0.6% in CFP-YFP cameleon cells following YFP bleaching (FIG. 1C). The CFP fluorescence did not increase appreciably in negative control pairs.

To measure FRET in live cells, the same pairs of fluorescent proteins were transiently expressed in HEK293 cells. In live HEK293 cells, FRET occurs in CFP-YFP cameleon cells and CFP-Bcl-2+YFP-IP$_3$R cells, but not in control cells. These results, although less quantitative than those obtained with the acceptor photobleaching method (Piston and Kremers, 2007, Trends Biochem. Sci. 32, 407-414), indicate that FRET occurs, providing evidence that the Bcl-2-IP$_3$R interaction exists not only in fixed cells, but also in living cells.

To summarize, taking into consideration technical limitations of FRET, measurements of FRET in both fixed and live cells indicate that Bcl-2 interacts with IP$_3$Rs in intact cells, verifying the interaction predicted by coimmunoprecipitation of these proteins from cell extracts.

Example 2

Endogenous Bcl-2 Interacts with IP$_3$R and Inhibits TCR-Mediated Ca$^{2+}$ Elevation Jurkat cells were used to test if endogenous Bcl-2 interacts with IP$_3$Rs and regulates TCR-mediated Ca$^{2+}$ elevation. The level of endogenous Bcl-2 in Jurkat cells is much less than that of exogenously expressed Bcl-2 in WEHI7.2 cells [Bcl-2(+) WEHI7.2 cells] (FIG. 2A). Nevertheless, Bcl-2 in Jurkat cells also coimmunoprecipitated with IP$_3$Rs (FIG. 2B), and siRNA-mediated knockdown of this Bcl-2 (FIG. 2C) enhanced anti-CD3-induced Ca$^{2+}$ elevation (FIGS. 2D and 2E), indicating the regulatory action of Jurkat cell Bcl-2 on IP3-mediated Ca$^{2+}$ elevation. Also, siRNA-mediated knockdown of Bcl-2 in Jurkat cells did not alter thapsigargin-induced Ca$^{2+}$ elevation (FIGS. 2F and 2G), suggesting that reducing the level of endogenous Bcl-2 did not affect ER Ca$^{2+}$ concentration, a finding consistent with earlier indirect and direct measurements of ER Ca$^{2+}$ in Bcl-2-overexpressing WEHI7.2 cells.

To summarize, evidence that endogenous Bcl-2 in Jurkat T cells interacts with IP$_3$Rs and regulates IP3-mediated Ca$^{2+}$ elevation alleviates concern that the previously reported inhibition of TCR-induced Ca$^{2+}$ elevation by Bcl-2 might be secondary to either clonal selection or high Bcl-2 levels associated with exogenous expression. Moreover, these findings enable investigation of both exogenously and endogenously expressed Bcl-2 throughout the experiments that follow.

Example 3

Bcl-2 Interacts with the Regulatory and Coupling Domain of the IP$_3$R

The three IP$_3$R subtypes differ in terms of functional properties, expression patterns, and subcellular localization in different cell types. Each IP$_3$R monomer has a cytoplasmic region containing an IP3-binding and an inhibitory and coupling domain close to the N terminus and an internal regulatory and coupling domain between the IP3 binding and channel domains, while the C-terminal IP$_3$R tail includes a gatekeeper domain (FIG. 3A).

Figure 3:
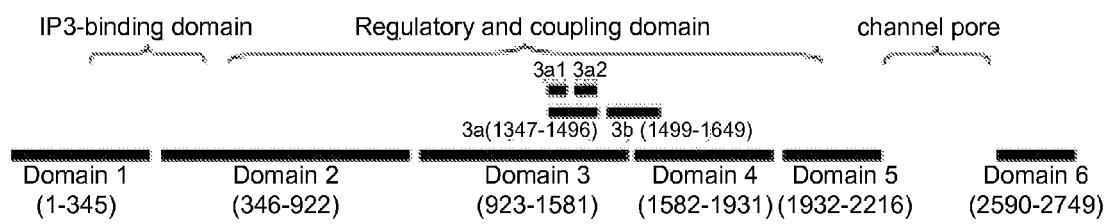
FIG. 3 illustrates Bcl-2-IP$_3$R Interaction Mapping Diagram of type 1 IP$_3$R domains.

To identify where Bcl-2 interacts on the IP$_3$R, we used a series of GST-IP$_3$R fusion constructs corresponding to five fragments covering the first N-terminal 2216 amino acids and 1 fragment corresponding to the last 160 amino acids of mouse IP$_3$R type 1 (FIG. 3). These fragments are located in the cytoplasm and coincide with "natural" domains generated by limited proteolysis. The transmembrane domain was not included. After purification, fragments migrated as single prominent bands corresponding to their expected molecular weights, although some minor degradation products were detected.

The first set of GST pull-down experiments utilized extracts of Bcl-2(+) WEHI7.2 cells and Jurkat cells as two independent sources of Bcl-2. Cell extracts were incubated with GST-IP$_3$R fragments prebound to glutathione sepharose resin, with equal loading of the GST-IP$_3$R fragments. After pull-down, Bcl-2 bound to IP$_3$R domains was detected by immunoblotting, indicating that Bcl-2 from each cellular source mainly interacted with IP$_3$R domain 3. These experiments were repeated a total of five times with the same result. It is important to note that, following incubation of cell extracts with GST-IP$_3$R fragments on the glutathione sepharose resin, the resin was washed extensively.

An interaction of Bcl-XL with domain 6 of IP$_3$R 1 was previously reported, but only three IP$_3$R fragments were tested: an N-terminal fragment (aa 1-600); a C-terminal fragment (aa 2512-2750); and a larger fragment, Δ1-600, encompassing both the regulatory and coupling domain and the C terminus. Thus, on the basis of these mapping studies a potential interaction of Bcl-XL/Bcl-2 within the regulatory and coupling domain was not formally tested. Also, the GST pull-down experiments employed stringency conditions lower than those in the present work. We therefore compared the interaction of Bcl-2 with domains 3 and 6 under three different buffer conditions, including the same buffer/wash conditions employed in our experiments described above (buffer 2), the buffer/wash condition employed by White et al. (2005, Nat. Cell Biol. 7, 1021-1028) (buffer 1), and a buffer employing CHAPS detergent (buffer 3) rather than the nonionic detergents employed in the other two buffers. The later control was included in view of earlier reports that nonionic detergents affect the Bcl-2 family member interactions (Hsu and Youle, 1997, J. Biol. Chem. 272, 13829-13837). With the lower stringency condition (buffer 1, 0.05% Triton, three times washing), domain 6 may interact with Bcl-2; however, under all three buffer conditions the interaction of domain 3 with Bcl-2 was much more prominent than the interaction of domain 6. Thus, it is possible that Bcl-2 interacts with both of these IP$_3$R regions, but because of the prominence of the interaction with domain 3, we choose to further analyze smaller fragments of domain 3, subdomains 3a (aa 1347-1496) and 3b (aa 1499-1649), to further narrow down the Bcl-2 binding region. These fragments correspond to smaller segments of the regulatory and coupling domain, as previously published (Sienaert et al., 1997, J. Biol. Chem. 272, 25899-25906) (FIG. 3). We found that Bcl-2 interacted with the 80 amino acid subdomain 3a1 (aa 1347-1426) most strongly. Therefore, this subdomain was targeted to develop an inhibitory peptide, and experiments employing this peptide further confirm the contribution of subdomain 3a1 to the interaction between Bcl-2 and IP$_3$R.

To address whether Bcl-2 associates with the IP$_3$R directly or not, GST pull-down experiments were performed using purified His-tagged full-length Bcl-2. This protein retains its ability to bind Bim and Bax. Our findings, confirmed in three separate experiments, indicate that the purified Histagged Bcl-2 also interacts with the GST-IP$_3$R domain 3 fragment. Thus, Bcl-2 directly interacts with the IP$_3$R in vitro.

In preliminary experiments, we found that deleting the BH4 domain from Bcl-2 prevented interaction of Bcl-2 with the IP$_3$R. We therefore screened a series of dicodon mutations in the BH4 domain and found that mutating amino acids 6 and 7 abrogated the Bcl-2-IP$_3$R interaction and abrogated Bcl-2's inhibition of anti-CD3-induced calcium elevation. These data indicate that the Bcl-2-IP$_3$R interaction is necessary for Bcl-2's inhibitory effect on calcium, a conclusion that is further substantiated by the following evidence using an inhibitory peptide that prevents the Bcl-2-IP$_3$R interaction.

Example 4

An IP$_3$R Peptide Inhibits Bcl-2-IP$_3$R Interaction

Figure 4:
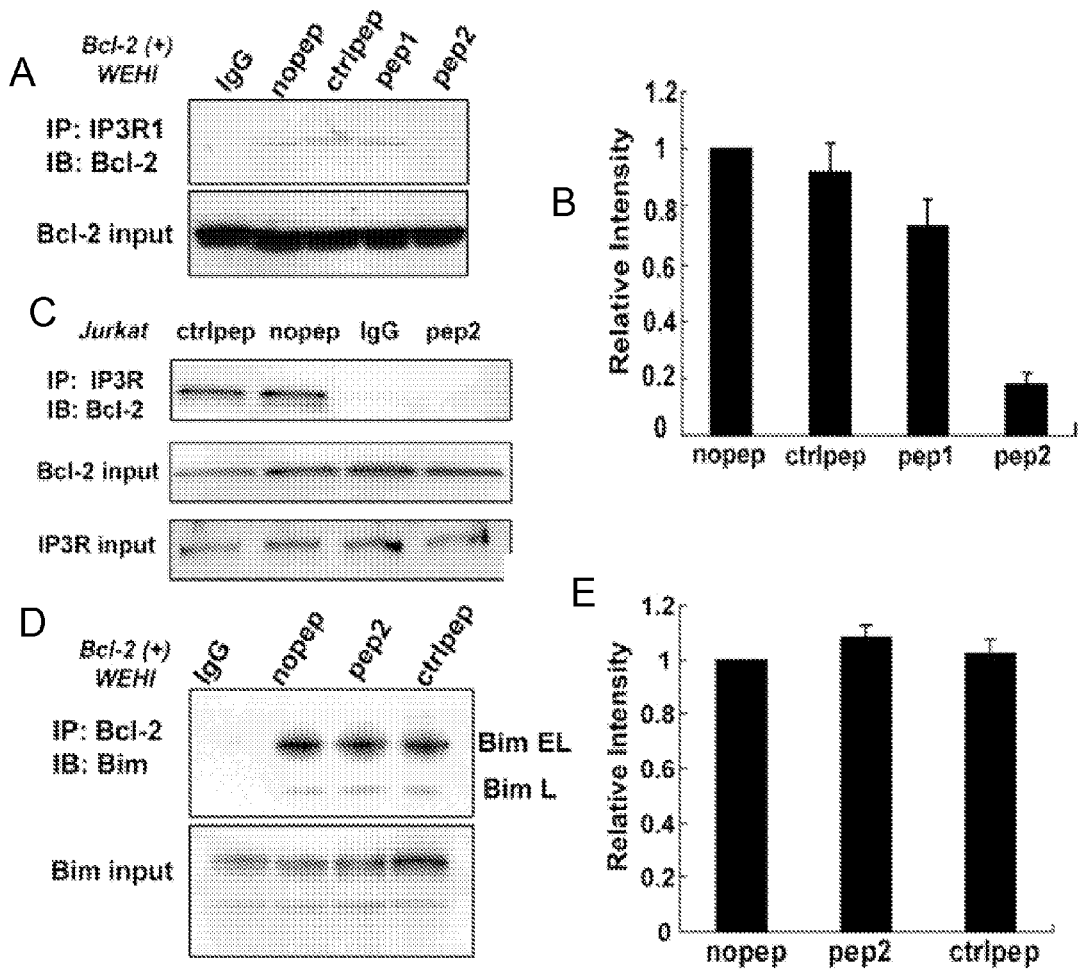
FIG. 4 illustrates an IP$_3$R Peptide Inhibits Bcl-2-IP$_3$R Interaction but Not Bim-Bcl-2 Interaction. (A and D) IP$_3$R was immunoprecipitated from extracts of Bcl-2(+) WEHI7.2 cells (C) or Jurkat cells in the presence of 400 µM peptides. Peptide 2, but not peptide 1 or control peptide, inhibited the Bcl-2-IP$_3$R coimmunoprecipitation. Summary of Bcl-2 immunoblot signal intensities in three GST pull-down experiments identical to (C) (mean±SEM). (B) Bcl-2 was immunoprecipitated from Bcl-2(+) WEHI7.2 cell extracts in the presence of 400 µM peptides, and coimmunoprecipitation of Bim was detected by anti-Bim immunoblotting. Neither control peptide nor peptide 2 interfered with the Bcl-2-Bim interaction. (E) Summary of Bim immunoblot signal intensities in three experiments identical to (B) (mean±SEM).

Since the IP$_3$R binding region was narrowed down to the 80 amino acid subdomain 3a1 (aa 1347-1426), we designed two 20 amino acid peptides (peptide 1, aa 1365-1384 (SEQ ID NO:2); peptide 2, aa 1389-1408 (SEQ ID NO:3)) based on the degree of homology in this region among different IP$_3$R isoforms. Also, preference was given to regions that have beta-turn and/or α-helical structures, rather than random-coil or nonstructured sequences, expecting that one or both of the peptides could inhibit the Bcl-2-IP$_3$R interaction. Furthermore, the C-terminal region of domain 3a1 was not selected because of its lower accessibility and unpredictable secondary structure (Invitrogen PeptideSelect Design Tool). The scrambled sequence of peptide 2 was also synthesized and used as a control. The effect of the peptides on Bcl-2-IP$_3$R interaction was initially tested in GST pull-down experiments using Bcl-2(+) WEHI7.2 extracts as a source of Bcl-2 (FIG. 4B). Peptides (200 μM and 1 mM) were incubated with Bcl-2(+) WEHI7.2 cell extracts and GSTIP$_3$R domain 3 attached to glutathione sepharose. The amount of bound Bcl-2 was significantly decreased by 200 μM or 1 mM peptide 2, but not by control peptide. At 1 mM, peptide 1 partially inhibited the interaction, but not as effectively as peptide 2. The inhibitory effect of peptide 2 on Bcl-2-IP$_3$R interaction was also detected in coimmunoprecipitation assays employing both Bcl-2(+) WEHI7.2 cells (FIGS. 4A and 4B) and Jurkat cells (FIG. 4C). Peptide 2 (400 μM) consistently inhibited Bcl-2-IP$_3$R interaction, whereas control peptide and peptide 1 did not inhibit the interaction (FIGS. 4A-4C). These results were confirmed in multiple experiments. As a control for specificity, peptide 2 disrupted Bcl-2-IP$_3$R interaction but not interaction of Bcl-2 with the BH3-only protein Bim (FIGS. 4D and 4E).

Example 5

Figure 5:
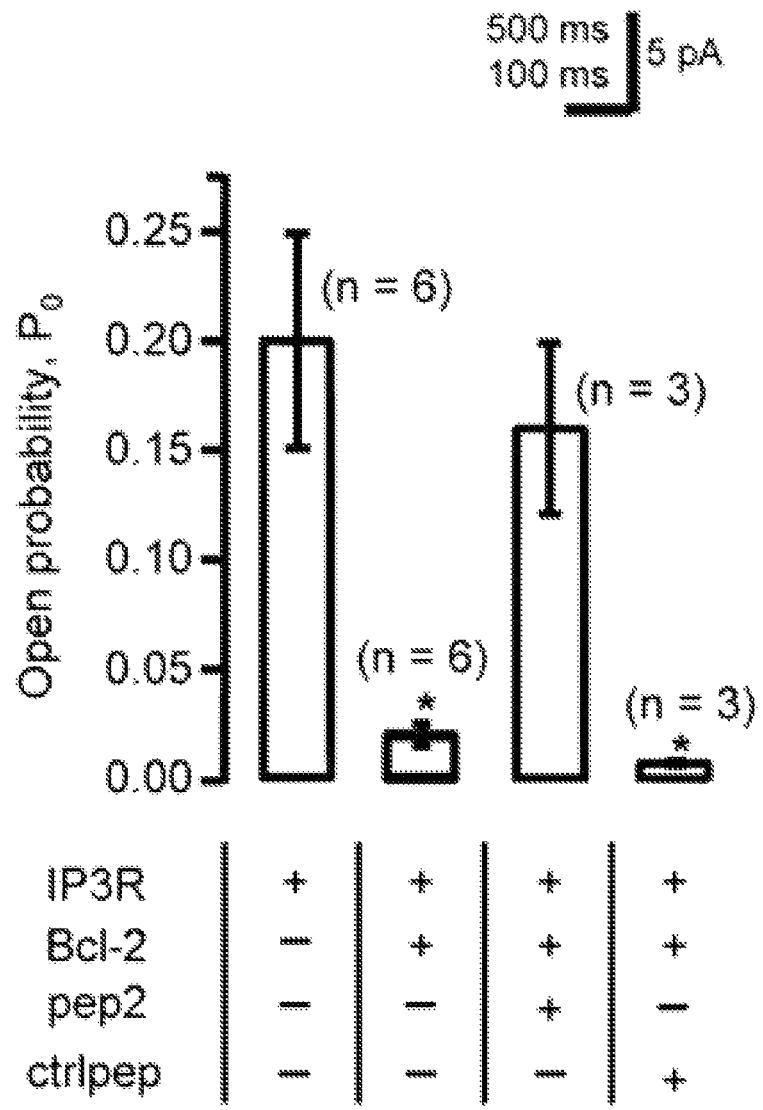
FIG. 5 illustrates a summary of multiple experiments (mean±SEM) measuring effects of Bcl-2 and peptides on IP$_3$R channel open probability. n=number of individual channels examined. Symbols represent mean±SEM. *$p<0.05$.

Peptide 2 Reverses Bcl-2's Inhibitory Effect on IP$_3$R Channel Opening In Vitro The effects of peptide 2 and purified Bcl-2 on IP$_3$R channel activity were analyzed in planar lipid bilayers under steady-state conditions. Single IP$_3$R type 1 channel activity was visualized as a series of discrete positive current fluctuations in the presence of 2 μM IP3 and 250 nM Ca$^{2+}$ in the cis compartment (cytoplasmic side of channel). A significant reduction in single channel activity was observed after adding 0.1 μM purified Bcl-2 to the cytoplasmic face of the IP$_3$R channel, and addition of 10 μM peptide 2 reversed Bcl-2's inhibitory effect on channel activity. Average open probabilities under various conditions were calculated from multiple repeated experiments (FIG. 5). Addition of Bcl-2 reduced IP$_3$R open probability by 11.5-fold to 0.018. Peptide 2 reversed Bcl-2's inhibitory effect, increasing the open probability back to 0.16, whereas control peptide did not reverse Bcl-2's inhibitory effect on channel activity (FIG. 5). These results demonstrate that peptide 2 reverses Bcl-2's inhibitory effect on IP$_3$R channel opening in a purified in vitro system, indicating that peptide 2 acts directly on the Bcl-2-IP$_3$R interaction to reverse Bcl-2's inhibitory effect on channel opening.

Example 6

Peptide 2 Reverses Bcl-2's Inhibitory Effect on TCR-Induced Ca$^{2+}$ Elevation

Next we investigated whether peptide 2 also reverses Bcl-2's inhibitory effect on Ca$^{2+}$ release through the IP$_3$R in Bcl-2(+) and (−) WEHI7.2 clones, newly derived WEHI7.2 mixed populations exogenously expressing Bcl-2, and Jurkat cells. Optimal conditions for peptide delivery and anti-CD3 concentration were determined in preliminary experiments. Peptide delivery in the lipid bilayer is 100%, whereas the penetration of peptide 2 into cells is much less, accounting for the lesser effect in cells. Therefore, a higher concentration of peptide (60 μM) was delivered into cells using the Chariot delivery reagent. Cytoplasmic Ca$^{2+}$ concentration was continuously measured at a single-cell level by digital imaging during anti-CD3 treatment. Representative Ca$^{2+}$ traces from Bcl-2(+) WEHI7.2 cells are shown in FIG. 6A, and the average Ca$^{2+}$ elevation induced by anti-CD3 in seven experiments is summarized in FIG. 6B. Observed variations in lag phase are at least partially attributable to the fact that lymphocytes are only loosely adherent to coverslips and thus rapid buffer exchange is not possible during antibody additions. Peptide 2 enhanced anti-CD3-induced Ca$^{2+}$ elevation in Bcl-2(+) WEHI7.2 cells by 40%. Control peptide and peptide 1 did not enhance anti-CD3-induced Ca$^{2+}$ elevation. In Bcl-2(−) cells, peptide 2 did not have a significant effect on Ca$^{2+}$ (FIG. 6B). Similarly, peptide 2 significantly enhanced anti-CD3-induced Ca$^{2+}$ elevation in Jurkat cells, whereas control peptide and peptide 1 did not (FIGS. 6C and 6D). Peptide 2 had no effect on Ca$^{2+}$ elevation when added to the cells in the absence of the Chariot reagent. Also, peptide 2 did not enhance anti-CD3-induced Ca$^{2+}$ elevation in Jurkat cells where the endogenous Bcl-2 level had been knocked down by siRNA, further confirming that the effect of peptide 2 on Ca$^{2+}$ is dependent upon its ability to disrupt the Bcl-2-IP$_3$R interaction. Additionally, peptide 2 did not affect intracellular Ca$^{2+}$ levels in the absence of anti-CD3 stimulation (data not shown). The low Bcl-2 level in Jurkat cells and the barely detectable endogenous Bcl-2 in Bcl-2(−) WEHI7.2 cells are consistent with the higher amplitude and longer duration of the Ca$^{2+}$ response in these cells in contrast to Bcl-2(+) WEHI7.2 cells (compare FIGS. 6A and 6B to FIGS. 6C and 6D). Thus, peptide 2 modulated anti-CD3-induced Ca$^{2+}$ elevation in both Bcl-2(+) WEHI7.2 cells and Jurkat cells, consistent with the ability of peptide 2 to disrupt Bcl-2-IP$_3$R interaction.

To exclude the possibility that peptide 2 may interfere with the upstream TCR activation pathway, a cell-permeant IP3 ester (D-myo InsP$_3$ hexakisbutyryloxymethyl ester) was used to bypass TCR activation and anti-CD3-induced IP3 generation. Peptide 2 enhanced IP$_3$ ester-induced Ca$^{2+}$ elevation in Jurkat cells, indicating that peptide 2 acts at the level of the IP$_3$R rather than interfering with upstream components of the TCR signaling pathway.

The conclusion that peptide 2 acts directly on the Bcl-2-IP$_3$R interaction is supported not only by experiments described above (FIG. 5) in which peptide 2 reversed Bcl-2-mediated inhibition of IP$_3$R channel opening in vitro, but also by unidirectional $^{45}$Ca$^{2+}$ flux experiments that allow for very accurate quantification of Ca$^{2+}$ release through IP$_3$Rs located on the ER. These experiments require firmly adherent cells, and therefore murine embryonic fibroblasts (MEFs), which have a somewhat lower level of endogenous Bcl-2 than Jurkat cells, were employed. The rate of IP3-induced $^{45}$Ca$^{2+}$ efflux was measured in the presence of thapsigargin, which completely prevents ER Ca$^{2+}$ reuptake. Peptide 2, but not control peptide, significantly increased the rate of $^{45}$Ca$^{2+}$ efflux, confirming that peptide 2 acts at the ER level to reverse Bcl-2's inhibition of IP$_3$R activity.

Example 7

Peptide 2 Enhances TCR-Induced Apoptosis

TCR-induced apoptosis is mediated by Ca$^{2+}$ release from the ER via the IP$_3$R, and as noted above, Bcl-2 inhibits TCR induced apoptosis by inhibiting IP3-mediated Ca$^{2+}$ release (Zhong et al., 2006, J. Cell Biol. 172, 127-137). Since peptide 2 reverses Bcl-2's inhibitory effect on Ca$^{2+}$ release, we next investigated whether peptide 2 also attenuates the inhibitory effect of Bcl-2 on anti-CD3-induced apoptosis. Peptides were delivered into Bcl-2(+) WEHI7.2 cells by Chariot reagent. After 3 hr, cells were treated with anti-CD3 antibody, and the percentage of apoptotic cells was measured 24 hr later. In Bcl-2(−) WEHI7.2 cells, anti-CD3 induced ~18% apoptotic cells while the Bcl-2-overexpressing Bcl-2(+) WEHI7.2 cells display markedly inhibited anti-CD3-induced apoptosis (FIG. 7B). Peptide 2 enhanced anti-CD3-induced apoptosis by 2-fold in Bcl-2(+) WEHI7.2 cells, whereas control peptide did not have a significant effect.

Figure 7A:
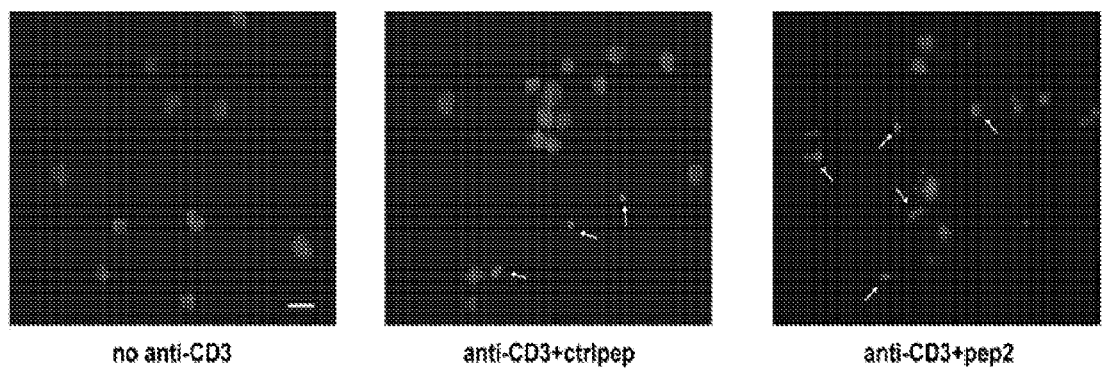

Peptide 2 also attenuated Bcl-2's inhibition of anti-CD3-induced apoptosis in Jurkat cells. In preliminary studies (data not shown), we tested several anti-CD3 concentrations. Higher concentrations of anti-CD3 induced high levels of apoptosis that might obscure the effect of the peptide. We therefore used 5 µg/ml anti-CD3, sufficient to induce 20%-30% apoptosis. Peptide 2 enhanced anti-CD3-induced apoptosis to 40%-45%, whereas the control peptide, peptide 1, or peptide 2 in the absence of Chariot reagent did not have an effect on anti-CD3-induced apoptosis (FIGS. 7A and 7C). In contrast to the effect of peptide 2 on anti-CD3-induced apoptosis, peptide 2 did not enhance Fas-induced $Ca^{2+}$-independent apoptosis in Jurkat cells.

In summary, consistent with the effects of peptide 2 on the Bcl-2-$IP_3R$ interaction and on anti-CD3-induced $Ca^{2+}$ elevation, peptide 2 enhanced anti-CD3-induced apoptosis in both Jurkat cells and Bcl-2(+) WEHI7.2 cells. In considering these findings, it is important keep in mind that Bcl-2 also inhibits apoptosis by binding to BH3-only proteins and that the effect of peptide 2 selectively interrupts Bcl-2-$IP_3R$ interaction, not the interaction of Bcl-2 with BH3-only proteins. Thus, it is to be expected that peptide 2 would only partially reverse Bcl-2's antiapoptotic activity.

Example 8

NMR Structure Analysis of BH4 Domain Accessible Amino Acids

The NMR structure of Bcl-2 was used identify amino acid residues on the surface of the BH4 domain that are accessible and to which peptide 2 binds and thus inhibits Bcl-2's interaction with the $IP_3R$.

FIG. 8 illustrates an NMR structure of Bcl-2 in accordance with an aspect of the invention. The amino acids that are accessible on the surface of the BH4 domain are shown. Atoms are shown as space-filling spheres; residues in the 4-28 stretch, which are conserved in the 7 closest homolog sequences are darker shaded, those which are not conserved are pale shaded. (Conserved: residues 4, 6-13, 15-19, 21, 23-26, and 28.)

FIG. 9 illustrates an NMR structure of Bcl-2 in accordance with another aspect of the invention. Atoms are shown as space-filling spheres; residues in the 4-28 stretch which are conserved in the 8 closest homolog sequences are darker shaded, those which are not conserved are in pale shaded. (Conserved: residues 6, 9-11, 13, 19, 21, 23, 25-26, and 28).

Based on these structures the amino acids most likely to be involved in the interaction of the BH4 domain of Bcl-2 (i.e., residues 4-28) with peptide 2 are pointed out below in Table 1 based on the relative surface accessibility of the side chains in residues 4-28 (side chains which high surface accessibility are exposed and available for specific binding to other molecules).

TABLE 1

| R4 | High | I17 | None |
|---|---|---|---|
| T5 | Low | H18 | High |
| G6 | No side chain | *Y19* | High |
| Y7 | Partial | K20 | Partial |
| D8 | High | L21 | Low |
| N9 | Partial | S22 | High |
| *R10* | High | *Q23* | High |
| E11 | Partial | R24 | High |
| I12 | None | G25 | No side chain |
| V13 | None | *Y26* | High |
| M14 | Partial | E27 | High |
| K15 | Partial | W28 | low |
| Y16 | Low | | |

Bolded if conserved in 7 closest sequences;
*Italic* if conserved in 8 closest sequences;
Underlined if conserved and has high accessibility.

Example 9

BH4 Domain Inhibiting Peptide and BH3 Domain Inhibiting Small Molecule Co-Therapy Since peptide 2 interacts with a different region of Bcl-2 than ABT737, we predict that peptide 2 may enhance the proapoptotic activity of ABT737. Thus, the concept is to target Bcl-2 at two different sites, both involved in apoptosis inhibition.

To test this hypothesis, we performed the experiments summarized below. The experimental design was to treat primary chronic lymphocytic leukemia cells (i.e., isolated from blood of patients and used immediately in experiments) with ABT737 alone, or in combination with a peptide 2 (SEQ ID NO: 3), and then to assess cell killing by trypan blue dye exclusion (dead cells fail to exclude this dye; hence, trypan blue positive cells are dead cells). Additions were made to CLL cells and cell death measured 24 hours later. (Note that killing of CLL cells by ABT737 has been reported previously by others.) FIGS. 10 and 11 indicate that peptide 2 having SEQ ID NO: 3 enhances cell death induction by ABT737.

From the above description of the invention, those skilled in the art will perceive improvements, changes and modifications. Such improvements, changes, and modifications are within the skill of the art and are intended to be covered by the appended claims. All patents, publications, and references cited in the present application are herein incorporated by reference in their entirety.

Having described the invention, we claim the following:

1. A purified peptide comprising a first amino acid sequence that includes about 10 to 80 amino acids, and a second amino acid sequence that facilitates transport of the purified peptide across a biological membrane, the first amino acid sequence having a sequence identity at least 90% homologous to about 10 to 80 consecutive amino acids of SEQ ID NO:1, the peptide inhibiting binding of Bcl-2 to $IP_3$ receptors ($IP_3R$) of cells that express $IP_3R$ and Bcl-2.

2. The purified peptide of claim 1, the peptide comprising a sequence selected from the group consisting of: SEQ ID NO:1, SEQ ID NO:2, and SEQ ID NO:3.

3. The purified peptide of claim 1 reversing the interaction of Bcl-2 with $IP_3R$ of cells that express $IP_3R$ and Bcl-2.

4. The purified peptide of claim 1, the peptide inhibiting binding of Bcl-2 to the activation coupling domain of $IP_3R$.

5. A pharmaceutical composition comprising:
a therapeutically effective amount of a peptide, the peptide including an amino acid sequence consisting of about 10 to 80 amino acids, the amino acid sequence having a sequence identity at least 90% homologous to about 10 to 80 consecutive amino acids of SEQ ID NO:1, the peptide inhibiting binding of Bcl-2 to $IP_3$ receptors ($IP_3R$) of cells that express $IP_3R$ and Bcl-2; and
a pharmaceutically effective carrier.

6. The pharmaceutical composition of claim 5, the peptide comprising a sequence selected from the group consisting of: SEQ ID NO:1, SEQ ID NO:2, and SEQ ID NO:3.

7. The pharmaceutical composition of claim 5, the peptide reversing the interaction of Bcl-2 with $IP_3R$ of cells that express $IP_3R$ and Bcl-2.

8. The pharmaceutical composition of claim 5, the peptide inhibiting binding of Bcl-2 to the activation coupling domain of $IP_3R$.

9. The pharmaceutical composition of claim 5, the peptide further comprising a second amino acid sequence that facilitates transport of the peptide across a biological membrane.

10. The pharmaceutical composition of claim 5, further comprising a second agent that inhibits binding of Bcl-2 to BH3 proapoptotic proteins.

11. The pharmaceutical composition of claim 10, the second agent comprising at least one of a chromene, a thiazolidine, a benzenesulfonyl, a benzenesulfonamide, an antimycin, a dibenzodiazocine, a terphenyl, an indole, gossypol, apogossypol, an epigallocatechingallate, or a theaflavin.

12. The pharmaceutical composition of claim 10, the second agent comprising N-(4-(4-(4'-chloro-biphenyl-2-ylmethyl)-piperazin-1-yl)-benzoyl)-4-(3-dimethylamino-1-phenylsulfanylmethyl-propylamino)-3-nitro-benzenesulfonamide or ABT-737.

* * * * *

SEQUENCE LISTING

<160> NUMBER OF SEQ ID NOS: 3

<210> SEQ ID NO 1
<211> LENGTH: 80
<212> TYPE: PRT
<213> ORGANISM: Homo sapiens

<400> SEQUENCE: 1

Glu Arg Asp Arg Met Asp Glu Asn Ser Pro Leu Met Tyr His Ile His
1               5                   10                  15

```
Leu Val Glu Leu Leu Ala Val Cys Thr Glu Gly Lys Asn Val Tyr Thr
            20                  25                  30

Glu Ile Lys Cys Asn Ser Leu Leu Pro Leu Asp Asp Ile Val Arg Val
            35                  40                  45

Val Thr His Glu Asp Cys Ile Pro Glu Val Lys Ile Ala Tyr Ile Asn
        50                  55                  60

Phe Leu Asn His Cys Tyr Val Asp Thr Glu Val Glu Met Lys Glu Ile
65                  70                  75                  80

<210> SEQ ID NO 2
<211> LENGTH: 20
<212> TYPE: PRT
<213> ORGANISM: Homo sapiens

<400> SEQUENCE: 2

Met Asp Glu Asn Ser Pro Leu Met Tyr His Ile His Leu Val Glu Leu
1               5                   10                  15

Leu Ala Val Cys
            20

<210> SEQ ID NO 3
<211> LENGTH: 20
<212> TYPE: PRT
<213> ORGANISM: Homo sapiens

<400> SEQUENCE: 3

Asn Val Tyr Thr Glu Ile Lys Cys Asn Ser Leu Leu Pro Leu Asp Asp
1               5                   10                  15

Ile Val Arg Val
            20
```